US007585928B2

(12) United States Patent  
Hefner, Jr.

(10) Patent No.: US 7,585,928 B2  
(45) Date of Patent: Sep. 8, 2009

(54) MULTIFUNCTIONAL MONOMERS CONTAINING BOUND MESOGENIC PORAGEN FORMING MOIETIES AND POLYARYLENE COMPOSITIONS THEREFROM

(75) Inventor: Robert E. Hefner, Jr., Lake Jackson, TX (US)

(73) Assignee: Dow Global Technologies, Midland, MI (US)

( * ) Notice: Subject to any disclaimer, the term of this patent is extended or adjusted under 35 U.S.C. 154(b) by 298 days.

(21) Appl. No.: 10/575,992

(22) PCT Filed: Oct. 19, 2004

(86) PCT No.: PCT/US2004/034329

§ 371 (c)(1),  
(2), (4) Date: Apr. 17, 2006

(87) PCT Pub. No.: WO2005/042613

PCT Pub. Date: May 12, 2005

(65) Prior Publication Data  
US 2007/0027278 A1 Feb. 1, 2007

(51) Int. Cl.  
C08G 61/02 (2006.01)  
C08J 9/26 (2006.01)

(52) U.S. Cl. .......................... 528/86; 521/61
(58) Field of Classification Search .................. 528/86  
See application file for complete search history.

(56) References Cited

U.S. PATENT DOCUMENTS

| | | | |
|---|---|---|---|
| 4,400,540 A | 8/1983 | Reinhardt et al. | |
| 5,189,117 A | 2/1993 | Hefner, Jr. | |
| 5,270,406 A | 12/1993 | Earls et al. | |
| 5,637,669 A | 6/1997 | Hefner, Jr. et al. | |
| 5,965,679 A | 10/1999 | Godschalx et al. | |
| 6,156,812 A | 12/2000 | Lau et al. | |
| 6,172,128 B1 | 1/2001 | Lau et al. | |
| 6,359,091 B1 | 3/2002 | Godschalx et al. | |
| 6,653,358 B2 | 11/2003 | Bruza et al. | |
| 6,828,406 B2 * | 12/2004 | Haasmann et al. | 528/86 |
| 6,887,910 B2 | 5/2005 | Bruza et al. | |
| 2003/0027970 A1 | 2/2003 | Haasmann et al. | |
| 2003/0083392 A1 | 5/2003 | Bruza et al. | |
| 2003/0165625 A1 | 9/2003 | So et al. | |
| 2004/0053033 A1 | 3/2004 | Niu et al. | |
| 2004/0054111 A1 | 3/2004 | Kalantar | |
| 2005/0014855 A1 | 1/2005 | Bruza | |

FOREIGN PATENT DOCUMENTS

| | | |
|---|---|---|
| EP | 1245586 A2 | 10/2002 |
| WO | WO-00/31183 | 6/2000 |
| WO | WO-03/068825 A2 | 8/2003 |
| WO | WO-03/070777 A1 | 8/2003 |
| WO | WO 2004/089862 | 10/2004 |
| WO | WO-2004/090018 A1 | 10/2004 |

OTHER PUBLICATIONS

Wiesler, U.-M., A. J. Berresheim, F. Morgenroth, G. Lieser, and K. Müllen, "Divergent Synthesis of Polyphenylene Dendrimers: The Role of Core and Branching Reagents upn Size and Shape", Macromolecules, 2001, pp. 187-199, vol. 34, No. 2.

Zhong, Ben et al., "Porous ultra low-k dielectrics having ultra small pores", Abstracts of Papers, 224th ACS National Meeting, Boston, MA, Aug. 18-22, 2002, Published by the American Chemical Society.

Chemical Abstract 2001:404713.  
Chemical Abstract 2003:570956.  
Chemical Abstract 2002:566264.  
Chemical Abstract 2000:133674.  
Chemical Abstract 1999:184247.

Ciferri, Albert ed., *Liquid Crystallinity in Polymers: Principles and Fundamental Properties*, Chapter 8. Liquid-Crystalline Sidechain Polymers. H. Finkelmann, pp. 315-340 (1991).

Baker, G. L. and J. K. Stille, "Hexaarylbenzene Units as Cross-Linking Sites for Polyquinolines", Macromolecules, 1979, pp. 369-373, vol. 12, No. 3.

Braham, J. N., T. Hodgins, T. Katto, R. T. Kohl, and J. K. Stille, "Polyphenylenes via Bis(2-pyrones) and Diethynylbenzenes. The Effect of m- and p- Phenlene Unites in the Chain", Macromolecules, 1978, pp. 343-346, vol. 11, No. 2.

Capek, Ignac and Jakub Chudej, "On the fine emulsion polymerization of styrene with non-ionic emulsifier," *Polymer Bulletin*, vol. 1999, 43, pp. 417-424.

Donescu et al., "The Influence of Monomers upon Microemulsions with Short Chain Cosurfactant," *J. Dispersion Science and Technology*, vol. 22, Nos. 2&3, pp. 231-244, 2001.

Feldman, Ken S., Robert E. Ruckle, Jr., Susan M. Ensel and Paul H. Weinreb, "Synthesis of a Chiral Binaphtyldisulfide: A Potentially Useful Reagent forCatalytic Asymmetric Syntheis", Tetrahedron, 1992, pp. 7101-7102, vol. 33, No. 47.

Gutsche et al., "Calixarenes. 6. Synthesis of a Functionalizable Calix[4]arene in a Conformationally Rigid Cone Conformation," *J. Am. Chem. Soc.*, vol. 104, pp. 2652-2653 (1982).

(Continued)

*Primary Examiner*—Mark Eashoo

(57) ABSTRACT

A compound (monomer) comprising i) one or more dienophile groups (A-functional groups), ii) one or more ring structures comprising two conjugated carbon-to-carbon double bonds and a leaving group L (B-functional groups), and iii) one or more chemically bound mesogenic poragen forming moieties, characterized in that the A-functional group is capable of reaction under cycloaddition reaction conditions with the B-functional group to thereby form a cross-linked, polyphenylene polymer.

5 Claims, No Drawings

OTHER PUBLICATIONS

Kraft, Arno et al., "Supramolecular liquid crystals with columnar mesophases through self-assembly of carboxylic acids around a tribasic core," *Chem. Comm*, pp. 1015-1016 (2000).

Kumar, Uday and Thomas X. Neenan, "Diels-Alder Polymerization between Bis(cyclopentadienones) and Acetylenes. A Versatile Route to New Hightly Aromatic Polymers", Macromolecules, 1995, pp. 124-130, vol. 28, No. 1.

Larpent, C. and T. F. Tadros, "Preparation of microlatex dispersions using oil-in-water microemulsions", Colloid Polmer Science, 1991, pp. 1171-1183, vol. 269, No. 11.

Lee, Hyung-Kun et al., "Synthesis of a Nanopourous Polymer with Hexagonal Channels from Supramolecular Discotic Liquid Crystals," *Angew. Chem. Int. Ed.*, vol. 40, No. 14, pp. 2669-2671 (2001).

Liu, Zhi, and Jerrold Meinwald, "5-(Trimethylstannyl)-2H-pyran-2-one and 3-(Trimethylstannyl)-2H-pyran-2-one: New 2H-Pyran-2-one Synthons", J. Org. Chem., 1996, pp. 6693-6699, vol. 61, No. 19.

McDonald et al., "Diels-Alder Reactivity of Oxygenated Dienes and Furans. Synthesis of Oxygenated Bipheynyls," *J. Chem. Soc. Perk. Trans.*, vol. 1, pp. 1893-1900, 1979.

Ogliaruso, Michael A. and Ernest I. Becker, "Bistetracyclones and Bishexaphenylbenzenes. II", *J. Org. Chem.*, 1965, pp. 3354-3360, vol. 30.

Ogliaruso, Michael A., Lewis A. Shadoff and Ernest I. Becker, "Bistetracyclones and Bishexaphenylbenzenes", *J. Org. Chem.*, 1963, pp. 2725-2728, vol. 28.

Puetter et al., *J. Prakt. Chem.*, 1951, vol. 149, pp. 183-216.

Schilling, Jr., Curtis L., Joe A. Reed, and J. K. Stille, "Diels-Alder Polymeriztions. VI. Phenylated Polyphenylenes from Bis-2-pyrones and p-Diethynylbenzene", Macromolecules, 1969, pp. 85-88, vol. 2, No. 1.

Tong, Ling, Douglas M. Ho, Nancy J. Vogelaar, Clarence E. Schutt, and Robert A. Pascal, Jr., "The Albatrossenes: Large, Cleft-Containing, Polyphenyl Polycyclic Aromatic Hydrocarbons", J. Am. Chem. Soc., 1997, pp. 7291-7302, vol. 119, No. 31.

Turchi, Stefania, Fodolfo Nesi, and Donatella Giomi, "Reactions of 4,5-Dicyanopyridazine with Alkynes and Enamines: a New Straghtforward Complementary Route to 4-Mono- and 4,5-Disubstituted Phthalonitriles", Tetrahedron, 1998, pp. 1809-1816, vol. 54.

Vankerckhoven, Henk F., Yvan K. Gilliams, and J. K. Stille, "Poly(p-phenylene). The Reaction of 5,5'-p-Phenylenebis-2-pyrone with p-Diethynylbenzene", Macromolecules, pp. 541-546, vol. 5, No. 5, 1972.

H. Warson, *The Applications of Synthetic Resin Emulsions*, 1972, p. 88.

* cited by examiner

MULTIFUNCTIONAL MONOMERS CONTAINING BOUND MESOGENIC PORAGEN FORMING MOIETIES AND POLYARYLENE COMPOSITIONS THEREFROM

This invention relates to compositions comprising bound mesogenic poragen forming moieties and having at least two different reactive functional groups and to aromatic polymers made from these monomers. More particularly, the invention relates to compositions comprising in a single monomer polyphenylene matrix forming functionality and a mesogenic poragen forming moiety. The resulting polymers are useful in making low dielectric constant insulating layers in microelectronic devices.

Polyarylene resins, such as those disclosed in U.S. Pat. No. 5,965,679 (Godschalx et al.) are low dielectric constant materials suitable for use as insulating films in semiconductor devices, especially integrated circuits. Such polyarylene compounds are prepared by reacting polyfunctional compounds having two or more cyclopentadienone groups with polyfunctional compounds having two or more aromatic acetylene groups, at least some of the polyfunctional compounds having three or more reactive groups. Certain single component reactive monomers which contained one cyclopentadienone group together with two aromatic acetylene groups, specifically 3,4-bis(3-(phenylethynyl)phenyl)-2,5-dicyclopentadienone and 3,4-bis(4-(phenylethynyl)phenyl)-2,5dicyclopentadienone, and polymers made from such monomers were also disclosed in the foregoing reference. Typically, these materials are b-staged in a solution and then coated onto a substrate followed by curing (vitrification) at elevated temperatures as high as 400-450° C. to complete the cure.

In U.S. Pat. No. 6,359,091, it was taught that it may be desirable to adjust the modulus of polymers as taught in Godschalx et al., by adjusting the ratio of the reactants or by adding other reactive species to the monomers or to the partially polymerized product of Godschalx et al. U.S. Pat. No. 6,172,128 teaches aromatic polymers containing cyclopentadienone groups that may react with aromatic polymers containing phenylacetylene groups to provide branched or cross-linked polymers. U.S. Pat. No. 6,156,812 discloses polymers which contain both cyclopentadienone- and phenylacetylene-backbone groups.

In WO 00/31183, cross-linkable compositions comprising a cross-linkable hydrocarbon-containing matrix precursor and a separate pore forming substance (poragen) which are curable to form low dielectric constant insulating layers for semiconductor devices were disclosed. By partially curing the precursor to form a matrix containing occlusions of the poragen and then removing the pore generating material to form voids or pores in the matrix material, lower dielectric constant insulating films may be prepared. It has now been discovered that the use of mixtures of a curable matrix resin and a separately added pore forming material, especially an ultra-small sized poragen, to form a b-staged polyphenylene resin formulation can suffer from poragen agglomeration, resulting in large diameter pore formation and an inhomogeneous distribution of pores, leading to variation in the electronic properties of the resulting film.

Although the foregoing advances have led to improvements in dielectric constant of the resulting film, additional improvements in film properties are desired by the industry. In particular, curable compositions capable of providing homogeneous, porous matrices by means of a single component are still desired. In addition, films and other cured compositions having improved physical properties, especially uniformly distributed, small pores, are sought.

Supramolecular liquid crystalline materials with hexagonal columnar mesophases that are self-assembled from long-chain alkoxybenzoic acids and a benzotri(imidazole) core through formation of intermolecular hydrogen bonds are known from *Chem. Commun.*, (2000), pg. 1015. Formation of a cross-linked polymer matrix by UV irradiation of a mixture of a photocurable monomer and a polymerizable supra-molecular discotic liquid crystal forming substance was disclosed in *Angew. Chem. Int. Ed.*, 40, 14 2669-2671 (2001). Upon chemical removal of the self-assembled columnar template, a nanoporous matrix containing hexagonal channels was formed. Compounds used to form mesogenic reagents for epoxide or polyurethane syntheses have been previously disclosed in U.S. Pat. Nos. 5,637,669 and 5,189,117.

According to a first embodiment of the present invention there is provided a compound (monomer) comprising i) one or more dienophile groups (A-functional groups), ii) one or more ring structures comprising two conjugated carbon-to-carbon double bonds and a leaving group L (B-functional groups), and iii) one or more chemically bound mesogenic poragen forming moieties, characterized in that the A-functional group is capable of reaction under cycloaddition reaction conditions with the B-functional group to thereby form a cross-linked, polyphenylene polymer.

According to a second embodiment of this invention, there is provided a curable oligomer or polymer made by the partial reaction of the A and B groups of the foregoing monomer, a mixture thereof, or a composition comprising the same under cycloaddition reaction conditions. In this embodiment of the invention the curable oligomer or polymer comprises some remainder of the two reactive A and B functional groups as pendant groups, terminal groups, or as groups within the backbone of the oligomer or polymer.

According to a third embodiment of the invention, there is provided a crosslinked polymer made by curing and crosslinking the foregoing curable monomers, oligomers or polymers of the first or second embodiments, or compositions comprising the same. Desirably, the resulting cross-linked polymers contain moieties formed through self-assembly of bound mesogenic poragen forming moieties that are homogeneously distributed throughout the polymer.

According to a fourth embodiment of the invention there is provided a process for making a porous, solid article comprising a vitrified polyarylene polymer which process comprises providing the foregoing curable monomers or oligomers of the first through third embodiments, or polymers or compositions comprising the same; partially polymerizing the monomer under cycloaddition reaction conditions optionally in the presence of a solvent and/or one or more separately added poragens, thereby forming a curable oligomer or polymer containing composition comprising self-ordered moieties formed through self-assembly of bound mesogenic poragen forming moieties; and curing and crosslinking the composition to form a solid polyarylene polymer containing such self-assembled regions of bound mesogenic poragen forming moieties and optionally separately added poragens. In a further step, the optional solvent, self assembled poragen regions, and/or separately added poragens may be removed.

In a fifth embodiment, this invention is an article made by the above method, desirably a porous article formed by removal of self-assembled, poragen regions and/or separately added poragens. Desirably, said article contains a homogeneous distribution of pores. Even more desirably, the pores are uniformly shaped due to the self-assembly properties of the bound mesogenic poragen forming moieties.

According to a sixth embodiment of the invention, the foregoing article is a film or a construct such as a semiconductor device, incorporating the film as an insulator between circuit lines or layers of circuit lines therein.

The monomers are highly soluble in typical solvents used in fabrication of semiconductor devices, and may be employed in formulations that are coated onto substrates and vitrified to form films and other articles. The compositions are desirable in order to obtain films having uniformly distributed small pores having a reduced potential for pore collapse or coalescence, and accordingly uniform electrical properties, and low dielectric constants. The films are stable at high temperatures and contain uniformly shaped, small average pore size, uniformly sized pores.

For purposes of United States patent practice, the contents of any patent, patent application or publication referenced herein is hereby incorporated by reference in its entirety herein, especially with respect to its disclosure of monomer, oligomer or polymer structures, synthetic techniques and general knowledge in the art. If appearing herein, the term "comprising" and derivatives thereof is not intended to exclude the presence of any additional component, step or procedure, whether or not the same is disclosed herein. In order to avoid any doubt, all compositions claimed herein through use of the term "comprising" may include any additional additive, adjuvant, or compound, unless stated to the contrary. In contrast, the term, "consisting essentially of" if appearing herein, excludes from the scope of any succeeding recitation any other component, step or procedure, excepting those that are not essential to operability. The term "consisting of", if used, excludes any component, step or procedure not specifically delineated or listed. The term "or", unless apparent from the context or stated otherwise, refers to the listed members individually as well as in any combination.

As used herein the term "aromatic" refers to a polyatomic, cyclic, ring system containing $(4\delta+2)$ 90 -electrons, wherein $\delta$ is an integer greater than or equal to 1. The term "fused" as used herein with respect to a ring system containing two or more polyatomic, cyclic rings means that with respect to at least two rings thereof, at least one pair of adjacent atoms is included in both rings.

"A-functionality" refers to a single dienophile group.

"B-functionality" refers to the ring structure comprising two conjugated carbon-to-carbon double bonds and a leaving group L.

"b-staged" refers to the oligomeric mixture or low molecular weight polymeric mixture resulting from partial polymerization of a monomer or monomer mixture. Unreacted monomer may be included in the mixture.

"Cross-linkable" refers to a matrix precursor that is capable of being irreversibly cured, to a material that cannot be reshaped or reformed. Cross-linking may be assisted by thermal, UV, microwave, x-ray, or e-beam irradiation.

"Dienophile" refers to a group that is able to react with the conjugated, double bonded carbon groups according to the present invention, preferably in a cycloaddition reaction involving elimination of the L group and aromatic ring formation.

"Inert substituent" means a substituent group which does not interfere with any subsequent desirable polymerization reaction of the monomer or b-staged oligomer and does not include further polymerizable moieties as disclosed herein.

"Matrix precursor" means a monomer, prepolymer, polymer, or mixture thereof which upon curing or further curing forms a cross-linked polymeric material.

"Monomer" refers to a polymerizable compound or mixture thereof.

"Matrix" refers to a continuous phase surrounding dispersed regions of a distinct composition or void.

"Mesogen" refers to a moiety or substituent of a monomer, oligomer or polymer herein that is capable of forming liquid crystal phases by self-assembly of similar moieties from other monomers, oligomer or polymers or from separately added mesogenic compounds. Both rod-like mesogens that form essentially a linear assemblage and discotic mesogens that form planar or multidimensional arrays are included. Preferred mesogens are discotic mesogens.

"Poragen" refers to polymeric or oligomeric components that may be combined with the monomers, oligomers, or polymers of the invention, and which may be removed from the initially formed oligomer or, more preferably, from the vitrified (that is the fully cured or cross-linked) polymer matrix, resulting in the formation of voids or pores in the polymer. Poragens may be removed from the matrix polymer by any suitable technique, including dissolving with solvents or, more preferably, by thermal decomposition. A "bound poragen" refers to a poragen that is chemically bound or grafted to the monomer, oligomer, or vitrified polymer matrix. A "bound, mesogenic, poragen forming moiety" refers to a bound functional group or moiety that is capable of forming a supramolecular complex or region by self-assembly or association of such species contained on adjacent monomers or regions of the same monomer, a partially cured or a b-staged oligomer thereof, or with separately added, non-polymerizable mesogenic compounds, which supramolecular complex is capable of subsequent removal from the fully cured polymer, thereby leaving a void. The self-assembly process may result from hydrogen bonding, polarity matching, or other self-ordering, template forming process between such moieties.

The Monomers and Their Syntheses

Preferred B-functional groups comprise cyclic, five-membered, conjugated diene rings where L is —O—, —S—, —C(O)—, or —(SO$_2$)—, or a six membered, conjugated diene ring where L is —N=N—, or —OC(O)—. Optionally, two of the carbon atoms of the ring structure and their substituent groups taken together may also form an aromatic ring, that is, the 5 or 6 membered ring structures may be part of a fused, multiple aromatic ring system.

Most preferably, L is —C(O)— such that the ring is a cyclopentadienone group or benzcyclopentadienone group. Examples of such most preferred cyclopentadienone rings are those containing aryl groups at the 2, 3, 4, or 5 positions thereof, more preferably at the 2, 3, 4 and 5 positions thereof.

Preferred dienophile groups (A-functionality) are unsaturated hydrocarbon groups, most preferably ethynyl or phenylethynyl groups.

The monomers of the present invention preferably comprise one or more dienophilic functional groups, preferably an arylacetylenic group; one or more hydrocarbon- or heteroatom substituted hydrocarbon- rings having two conjugated carbon to carbon double bonds and the leaving group, L; one or more bound mesogenic poragen forming side chains; and, optionally, inert substituents. Desirably, the mesogenic poragen forming moieties are bound to a moiety comprising a B-functionality, an A-functionality, or both B- and A-functionalities through any group capable of covalently binding said mesogenic poragen forming moieties to those moieties comprising B- and/or A-functionalities. Examples of suitable covalent linking groups include saturated and unsaturated hydrocarbon chains, keto (—CO—) groups, ethers, esters, amides, carbonates, urethanes and ureas.

In a preferred embodiment, the covalent linking group comprises a multiatomic group that acts as a flexible spacer between the mesogenic poragen forming moiety and remainder of the monomer. By the term "flexible" is meant a group able to alleviate translational and/or rotational restriction of the mesogenic group to impart molecular mobility needed to undergo association between mesogen forming chains as disclosed in Chapter 8, "Liquid-Crystalline Sidechain Polymers", in *Liquid Crystallinity in Polymers Principles and Fundamental Properties*, Albert Ciferri, ed. VCH Publishers, Inc. (1991). Examples of suitable flexible spacer groups include aliphatic $C_{2-10}$ hydrocarbyl-, hydrocarbyloxy- and poly(hydrocarbyloxy)-groups.

Representative rod-like mesogenic moieties include groups containing a single aromatic terminal group as well as those containing one or more divalent, single or multiple ring, aromatic ligands, connected by one or more rigid linking groups. The bound, rod-like mesogenic poragen forming moieties may be generally represented by the formula:

—(CLG)-(DArL-RCL-)$_m$-(MArL), where CLG is the covalent linking group, DArL is a divalent aromatic ligand, RCL is a rigid central linkage, MArL is a monovalent aromatic terminal ligand, and m has a value of zero to 100.

Preferred DArL groups are para-substituted single or multiple fused ring aromatic groups. Representative examples include:

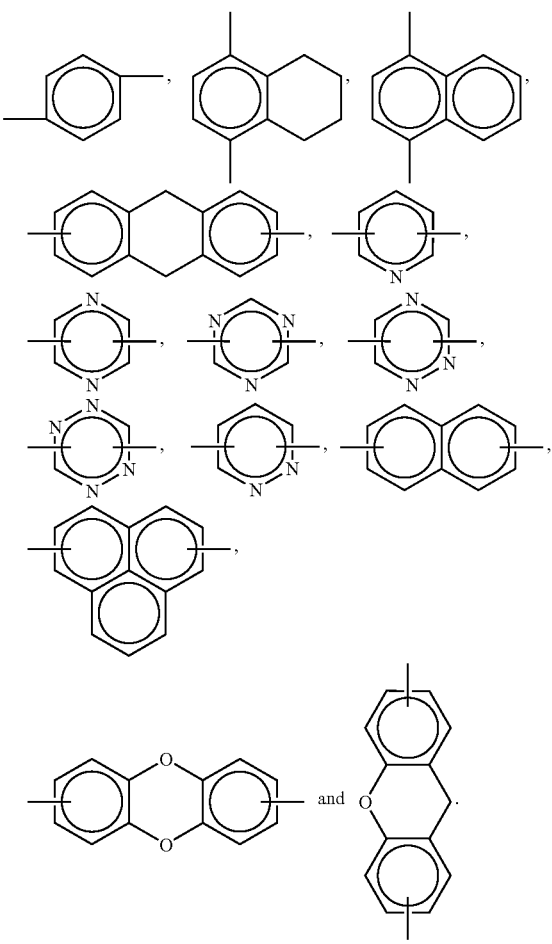

Phenylene rings are the most preferred DArL groups.

Suitable monovalent aromatic terminal ligands are derived from the foregoing divalent ligands by loss of one of the bonds thereto. A preferred MArL is phenyl.

Suitable rigid central linkages (RCL's) are those that minimize rotation, folding or bending of the mesogenic components or aromatic rings thereof, thereby maintaining a "rod-like" shape needed for mesogenicity. The presence of rigid central linkages may be determined via conventional methods such as NMR, MS, or IR analysis, as well as by the presence of mesogenicity (liquid crystallinity) as determined by the presence of thermal transitions of the nematic and/or smectic phases in the heating and cooling scan determined by differential scanning calorimetry (DSC), as well as visable appearance (under cross-polarized light on a heated microscope stage) or X-ray evidence of transition into and out of nematic and/or smectic phases.

Suitable rigid central linkage groups include the following: a direct single bond, —C≡C—, —CR$^5$=N—, —N=N—, —C(O)O—, —NR$^5$—C(O)—, —CR$^5$=N—N=CR$^5$—, —CR$^5$=CR$^5$—C(O)—O—CH$_2$—, —CR$^5$=CR$^5$—, —C(O)—NR$^5$—, —CH$_2$—O—C(O)—CR$^5$=CR$^5$—, —C(O)O—N=CR$^5$—, —CR$^5$=N—OC(O)—, —C(O)—NR$^5$—NR$^5$—C(O)—, —CR$^5$=CR$^5$—OC(O), —C(O)O—CR$^5$=CR$^5$—, —OC(O)—CR$^5$=CR$^5$—, —CR$^5$=CR$^5$—C(O)O—, —CHR$^5$—OC(O)—CR$^5$=CR$^5$—, —CR$^5$=CR$^5$—C(O)O—CHR$^5$—, —CHR$^5$—C(O)O—CR$^5$=CR$^5$—, —CR$^5$=CR5—OC(O)—CHR$^5$—, —C(O)—S—, —CH$_2$—CH$_2$—C(O)O—, —OC(O)CH$_2$—CH$_2$—, —C≡C—C≡C—, —CR$^5$=CR$^5$—CR$^5$=CR$^5$—, —CR$^5$=CR$^5$—C(O)—O—CH$_2$—CH$_2$—, —CH$_2$—CH$_2$—O—C(O)—CR$^5$=CR$^5$—, —CR$^5$=C(—C≡N)—, —(N=C—)C=CR$^5$—, —CR$^5$=C(Cl)—, —(Cl)C=CR$^5$—, —N=C(—C≡N)—, —(N=C—)C=N—,

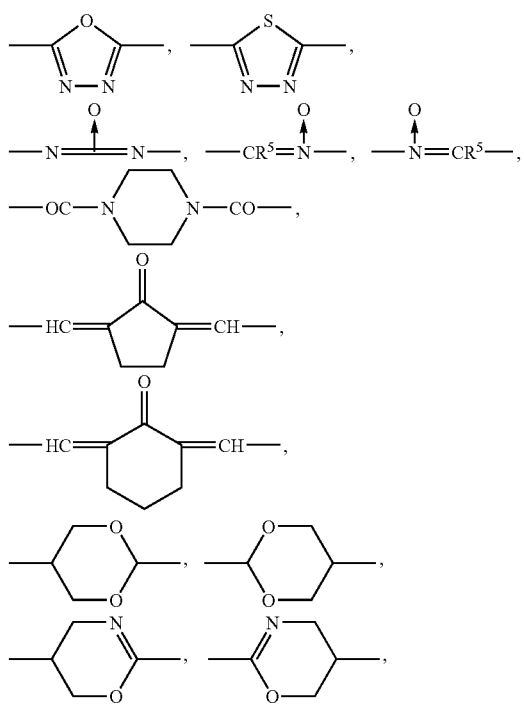

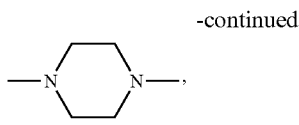

or divalent groups of the formula -A-Z-A-, wherein: A, independently at each occurrence is —OC(O)—, —C(O)O—, —NR⁵C(O)—, or —C(O)—NR⁵—; and Z is:

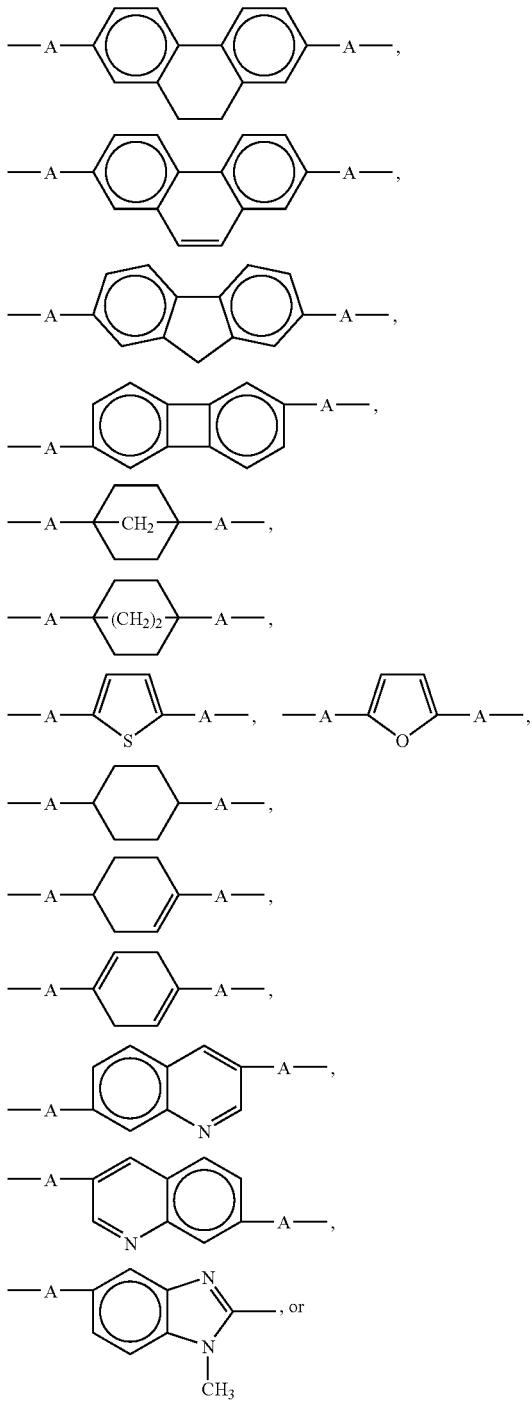

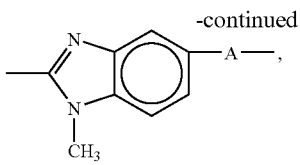

and $R^5$ is H or $C_{1-4}$ alkyl.

Preferred rod-like mesogenic poragen forming moieties are those which may be removed from the matrix polymer by thermal decomposition and do not possess structure capable of reacting appreciably with the A- or B-functional groups at the temperature employed for the thermal decomposition.

The bound discotic mesogenic poragen forming moieties may be generally represented by the formula: —(CLG)-D, where CLG is the covalent linking group and D is the discotic mesogenic moiety or a series of two or more covalently bound discotic moieties.

Preferred discotic mesogenic poragen forming moieties are polyatomic moieties comprising an essentially planar, rigid core in the form of a disk, polygon, or other closed shape, optionally substituted with one or more aliphatic or aromatic appendages or functional groups. Preferred discotic moieties are derivatives of a core having from 10 to 100 atoms, not counting hydrogen, that is selected from the group consisting of: triphenylenes, azatriphenylenes, hexa(4-substituted benzoates) of triphenylene, alkyl or substituted alkyl pentakis(phenylethynyl)phenyl ethers, multi((phenyl)alkynyl)triphenylenes, hexakis((phenyl)alkynyl)benzenes, hexakis((phenyl)alkynyl)naphthalenes, hexa(4-substituted benzoates) of benzene, hexakis(aryloxy)benzenes, truxenes, trithiatruxenes, trioxatruxenes, triazatruxenes, triketotruxenes, phthalocyanines, metallophthalocyanines, porphyrins, metalloporphyrins, macrocyclic polyamines, cyclomultibenzylenes, metacyclophanes, anthraquinones, tricycloquinazoline, bipyranylidenes, triptycenes, bis[1,2-bis(phenyl)ethane-1,2-dithiolato]metals, bis(5-diketonato) metal complexes, triaryl pyrylium salts, decacyclenes, dibenzopyrenes, tungsten-oxocalix[4]arenes and cis,cis-(3,5-dihydroxycyclohexyl)-3,4,5-tri(substituted)benzoates.

Representative discotic mesogenic poragen forming moieties may be derived from compounds and complexes including, for example, the hexalis(substituted)benzenes, such as 1,2,3,4,5,6-hexamethylbenzene, 1,2,3,4,5,6-hexacarboxybenzene, 1,2,3,4,5,6-hexamercaptobenzene, 1,2,3,4,5,6-hexa-N-methylaminobenzene; the triphenylenes, such as 2,3,6,7,10,11-hexamethyltriphenylene, 2,3,6,7,10,11-hexacarboxytriphenylene, 2,3,6,7,10,11-hexamercaptotriphenylene, 2,6,10-trimethyl-3,7,11-trimethoxytriphenylene, 2,6,10-trimethoxy-3,7,11-trimethyltriphenylene, 2-methyl-3,6,7,10,11-pentamethoxytriphenylene, 2-methoxy-3,6,7,10,11-pentamethyltriphenylene, 2,6,10-trimethyl-3,7,11-tridodecyloxytriphenylene, 2,6,10-trimethyltriphenylene, 3,7,11-trimethyltriphenylene, 2,6,10-trimethyl-3,6,7-trimethyltriphenylene, 3,7,11-trimethyl-2,6,10-trimethyltriphenylene, 3,6,7,11-tetramethyl-2,10-triphenylenediacetate, 3,6,10,11-tetramethyl-2,7-triphenylenediacetate, 3,6,7,10-tetramethyl-2,11-triphenylenediacetate, 3,6,7,11-tetramethyl-2,10-triphenylenedistearate, 3,6,7,11-tetracarboxy-2,10-triphenylenediacetate, 2,3,6,7,10,11-tris(N,N'-ethylenediamino)triphenylene, 2,3,6,7,10,11-tris(N-methyl, N'-ethylenediamino)triphenylene, 1,5,9-trihexyl-2,3,6,7,10,11-tris(N,N'-ethylenediamino) triphenylene; the azatriphenylenes, such as 2,3,6,7,10,11-hexamethyl-1,5,9-triazatriphenylene, 2,3,6,7,10,11-hexacarboxy-1,5,9-triazatriphenylene, 2,6,10-triethyl-1,5,9-triazatriphenylene, 2,6,10-trimethyl-3,7,11-trihexyl-1,5,9-triazatriphenylene, 2-methyl-3,6,7,10,11-pentamethoxy-1,5,9-triazatriphenylene, 3,7,11-trimethyl-2,6,10-triazatriphenylene, 2,6,10-trimethyl-3,7,11-triazatriphenylene, 2,3,6,7,10,11-hexamethyl-1,4,5,8,9,12-hexaazatriphenylene, 2,3,6,7,10,11-hexacarboxy-1,4,5,8,9,12-hexaazatriphenylene; the multi (phenyl)alkynyltriphenylenes, such as 2,3,6,7,10,11-hexakis((4-methylphenyl)ethynyltriphenylene, 2,6,10-tris((4-methylphenyl)ethynyltriphenylene, 3,7,11-trimethoxy-2,6,10-tris((4-methylphenyl)ethynyltriphenylene; the alkyl or substituted alkyl pentakis(phenylethynyl)phenyl ethers, such as 11-(pentakis((4-methylphenyl)ethynyl)-phenoxy)undecane, 11-(pentakis((4-methylphenyl)ethynyl)phenoxy)undecanoic acid ethyl ester; the hexakis((phenyl)alkynyl)benzenes and the hexakis((phenyl)alkynyl)naphthalenes, such as hexakis((4-methylphenyl)ethynyl)benzene,hexakis((3,5-dimnethyl-4-methylph enyl)ethynyl)benzene, 1,2,3,5,7-hexakis((4-methylphenyl)ethynyl)naphthalene; the hexakis (aryloxy)benzenes such as hexakis(4-methylphenyloxy)benzene, hexakis(3,5-dimethyl-4-methylphenyloxy)benzene; the truxenes such as 2,3,7,8,12,13-hexamethyltruxene, 2,3,7,8,12,13-hexamercaptotruxene, 2,3,7,8,12,13-hexacarboxytruxene, 2,3,7,8,12,13-hexa-N-methylaminotruxene, 2,7,12-trimethyltruxene, 3,8,13-trimethyltruxene, 2,7,12-trimethyl-3,8,13-trimethyltruxene, 2,7,12-trimethyl-3,8,13-triacetoxytruxene, 2,7,12-trimethyl-3,8,13-trimethyltruxene, 2-methyl-3,7,8,12,13-pentamethyltruxene, 2,8-dimethyl-3,7,12,13-tetramethyltruxene, 1,6,11-trimethyl-3,8,13-trimethyltruxene; the trithiatruxenes such as 2,3,7,8,12,13-hexamethyl(1,2-b; 3,4-b'; 5,6-b")trisbenzothiophene, 2,3,7,8,12,13-hexacarboxy(1,2-b; 3,4-b'; 5,6-b") trisbenzothiophene, 2,3,7,8,12,13-hexamercapto(1,2-b; 3,4-b'; 5,6-b")trisbenzothiophene, 2,3,7,8,12,13-hexa-N-methylamino(1,2-b; 3,4-b'; 5,6-b")trisbenzothiophene, 2,7,12-trimethyl(1,2-b; 3,4-b'; 5,6-b")trisbenzothiophene, 3,8,13-trimethyl(1,2-b; 3,4-b'; 5,6-b")trisbenzothiophene, 2,7,12-trihexyloxy-3,8,13-trimethyl(1,2-b; 3,4-b'; 5,6-b") trisbenzothiophene, 2,7,12-trihexyl-3,8,13-trimethyl(1,2-b; 3,4-b'; 5,6-b")trisbenzothiophene, 3,7,8,12,13-pentamethyl-2-methyl(1,2-b; 3,4-b'; 5,6-b")trisbenzothiophene, 3,7,12,13-tetramethyl-2,8-dimethyl(1,2-b; 3,4-b'; 5,6-b")trisbenzothiophene; the trioxatruxenes such as 2,3,7,8,12,13-hexamethyl(1,2-b; 3,4-b'; 5,6-b")trisbenzofuran, 2,3,7,8,12,13-hexacarboxy(1,2-b; 3,4-b'; 5,6-b")trisbenzofuran, 2,3,7,8,12,13-hexamercapto(1,2-b; 3,4-b'; 5,6-b")trisbenzofuran, 2,3,7,8,12,13-hexa-N-methylamino(1,2-b; 3,4-b'; 5,6-b") trisbenzofuran, 2,7,12-trimethyl(1,2-b; 3,4-b'; 5,6-b")trisbenzofuran, 3,8,13-trimethyl(1,2-b; 3,4-b'; 5,6-b")trisbenzofuran, 2,7,12-trihexyloxy-3,8,13trimethyl(1,2-b; 3,4-b'; 5,6-b")trisbenzofuran, 2,7,12-trihexyl-3,8,13-trimethyl(1,2-b; 3,4-b'; 5,6-b")trisbenzofuran, 3,7,8,12,13-pentamethyl-2-methyl(1,2-b; 3,4-b'; 5,6-b")trisbenzofuran, 3,7,12,13-tetramethyl-2,8-dimethyl(1,2-b; 3,4-b'; 5,6-b")trisbenzofuran; the triazatruxenes such as 2,3,7,8,12,13-hexamethyl(1,2-b; 3,4-b'; 5,6-b")trisbenzo-N-methylpyrrole, 2,3,7,8,12,13-hexamethyl(1,2-b; 3,4-b'; 5,6-b")trisbenzo-N-ethylpyrrole, 2,3,7,8,12,13-hexacarboxy(1,2-b; 3,4-b'; 5,6-b")trisbenzo-N-methylpyrrole, 2,3,7,8,12,13-hexamercapto(1,2-b; 3,4-b'; 5,6-b")trisbenzo-N-methylpyrrole, 2,3,7,8,12,13-hexa-N-methylamino(1,2-b; 3,4-b'; 5,6-b")trisbenzo-N-methylpyrrole, 2,7,12-trimethyl(1,2-b; 3,4-b'; 5,6-b")trisbenzo-N-methylpyrrole, 3,8,13-trimethyl(1,2-b; 3,4-b'; 5,6-b")trisbenzo-N-methylpyrrole, 2,7,12-trihexyloxy-3,8,13-trimethyl(1,2-b; 3,4-b'; 5,6-b")trisbenzo-N-methylpyrrole, 2,7,12-trihexyl-3,8,13-trimethyl(1,2-b; 3,4-b'; 5,6-b")trisbenzo-N-methylpyrrole, 3,7,8,12,13-pentamethyl-2-methyl(1,2-b; 3,4-b'; 5,6-b")trisbenzo-N-methylpyrrole, 3,7,12,13-tetramethyl-2,8-dimethyl(1,2-b; 3,4-b'; 5,6-b")trisbenzo-N-methylpyrrole; triketotruxenes, phthalocyanines, metallophthalocyanines, porphyrins and metalloporphyrins, macrocyclic polyamines, cyclomultibenzylenes, metacyclophanes, anthraquinones, tricycloquinazolines, bipyranylidenes, bithiopyranylidenes, triptycenes, bis[1,2-bis(phenyl)ethane-1,2-dithilato]metals, bis(betadiketonato)metal complexes, (N-(4-methyl, alkoxy or alkyl substituted salicylidene)4'-methyl, alkoxy or alkyl substituted aniline) copper (II) complexes, triaryl pyrylium salts, decacyclenes, dibenzopyrenes, tungsten-oxocalix[4]arenes, and cis,cis-(3,5-dimethylcyclohexyl)-3,4,5-tri(substituted)benzoates.

The foregoing and related compounds and their preparations are disclosed in U.S. Pat. Nos. 5,637,669 and 5,189,117.

The molecular weight of the bound mesogenic poragen forming moiety and the resultant effective molecular weight formed by the self-assembly of bound poragen forming moieties directly relate to the size of the pore left after removal of the self-assembled poragen regions. Thus, it is highly desirable to adjust the molecular weight of the bound mesogenic poragen forming moiety to produce the desired pore size in the solid polyarylene polymer. The molecular weight of the mesogenic poragen forming moiety may be increased by covalently connecting two or more identical or dissimilar rod-like or discotic mesogenic moieties together. Molecular weights of the mesogenic poragen forming moiety of from 400 to 10,000 amu are generally preferred, with molecular weights from 1000 to 4000 being most preferred. The number of bound mesogenic poragen forming moieties present may be adjusted to decrease or increase the number and distribution of pores in the solid polyarylene polymer.

The monomers of the present invention may be depicted generically by the formula: AxByMz, wherein A, B and M stand for A-functionality, B-functionality and bound mesogenic poragen forming moieties respectively, and x, y and z are integers greater than or equal to one. More preferably, x is greater than or equal to 2, and y and z are greater than or equal to 2.

Examples of suitable monomers according to the invention are compounds corresponding to the formula,

(I)

wherein L is —O—, —S—, —N═N—, —C(O)—, —SO$_2$)—, or —OC(O)—;

Z is independently in each occurrence hydrogen, halogen, an unsubstituted or inertly substituted hydrocarbyl group, Z"X, or two adjacent Z groups together with the carbons to which they are attached form a fused aromatic ring, —Z" is a divalent derivative of an unsubstituted or inertly substituted hydrocarbyl group joining two or more structures of formula (I), or joining an A-functionality, a bound mesogenic poragen forming moiety, or a moiety comprising both an A-functionality and a bound mesogenic poragen forming moiety, X is a second structure of formula (I), a moiety comprising A-functionality, a group comprising a mesogenic poragen forming moiety, or a moiety comprising both an A-functionality and a mesogenic poragen forming moiety and in at least one occurrence, Z is a Z"X group of the formula: -Z"-C≡CM;

or in at least one occurrence, Z is a Z"X group of the formula: -Z"-C-CR and in at least one other occurrence Z is a Z"X group comprising a mesogenic poragen forming moiety; wherein, M is independently each occurrence a bound mesogenic poragen forming moiety; and R is independently each occurrence selected from the group consisting of hydrogen, $C_{1-4}$ alkyl, $C_{6-60}$ aryl, and $C_{7-60}$ inertly substituted aryl groups.

Preferred monomers according to the present invention are 3-substituted cyclopentadienone compounds or 3,4-disubstituted cyclopentadienone compounds, represented by the formula:

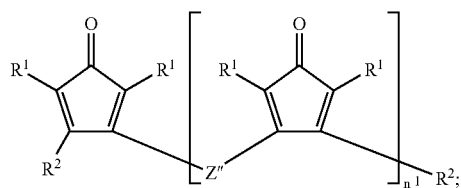

wherein $R^1$ independently each occurrence is $C_{6-20}$ aryl, $C_{6-20}$ inertly substituted aryl, or $R^2$;

$R^2$ is $C_{6-20}$ aryl-substituted ethynyl, -Z"-M, $C_{6-20}$ aryl, or $C_{6-20}$ inertly substituted aryl;

Z" is a divalent linking group, and

M is a bound mesogenic poragen forming moiety, $n^1$ is a number greater than or equal to zero;

with the proviso that in at least one occurrence $R^1$ or $R^2$ is $C_{6-20}$ aryl-substituted ethynyl, and in at least one other occurrence $R^1$ or $R^2$ is -Z"-M.

Examples of $R^1$ and $R^2$ groups include: $C_{6-20}$ aryl-substituted ethynyl, -Z"-M, —C≡C-M, $C_{6-20}$ aryl, or inertly substituted $C_{6-20}$ aryl, more preferably phenyl, biphenyl, p-phenoxyphenyl, naphthyl, or phenylethynyl.

Examples of suitable Z" groups include: phenylene, biphenylene, phenyleneoxyphenylene, ethynylene, -phenylene-$C_{1-12}$ alkylene-, -phenylene-O—$C_{1-12}$ alkylene-, -phenylene-$C_{1-12}$ alkylene-O—, -phenylene-O—$C_{1-12}$ alkylene-O—, -phenylene-CO—, -phenylene-O—, -phenylene-OC(O)—, -phenylene-C(O)O—, -phenylene-C(O)—NH—, -phenylene-NH—C(O)—, -phenylene-OC(O)O—, -phenylene-NHC(O)O—, -phenylene-OC(O)NH—, -phenylene-NHC(O)NH—, -phenylene-$C_{1-12}$ alkylene-C(O)O—, -phenylene-$C_{1-12}$ alkylene-C(O)NH—, -phenylene-$C_{1-12}$ alkylene-OC(O)—, -phenylene-$C_{1-12}$ alkylene-OC(O)NH—, -phenylene-$C_{1-12}$ alkylene-NHC(O)O—, -phenylene-$C_{1-12}$ alkylene-OC(O)O—, -phenylene-$C_{1-12}$ alkylene-NHC(O)NH—, -phenylene-O—$C_{1-12}$ alkylene-C(O)O—, -phenylene-O—$C_{1-12}$ alkylene-C(O)NH—, -phenylene-O—$C_{1-12}$ alkylene-OC(O)—, -phenylene-O—$C_{1-12}$ alkylene-OC(O)NH—, -phenylene-O—$C_{1-12}$ alkylene-NHC(O)O—, -phenylene-O—$C_{1-12}$ alkylene-OC(O)O— and -phenylene-O—$C_{1-12}$ alkylene-NHC(O)NH—.

Preferably M is a moiety capable of molecular self association with adjacent M moieties, more preferably a discotic mesogenic poragen forming moiety.

Synthesis of AxByMz Monomers

The monomers according to the present invention may be made by the reaction of diaryl-substituted acetone compounds with aromatic polyketones using conventional methods. Exemplary methods are disclosed in *Macromolecules*, 28, 124-130 (1995); *J. Org. Chem*, 30, 3354 (1965); *J. Org. Chem.*, 28, 2725 (1963); *Macromolecules*, 34, 187 (2001); *Macromolecules*, 12, 369 (1979); *J. Am Chem. Soc.* 119, 7291 (1997); and U.S. Pat. No. 4,400,540.

More preferably, the monomers may be made by the reaction of the following synthons, or molecular components, according to one of the following schemes:

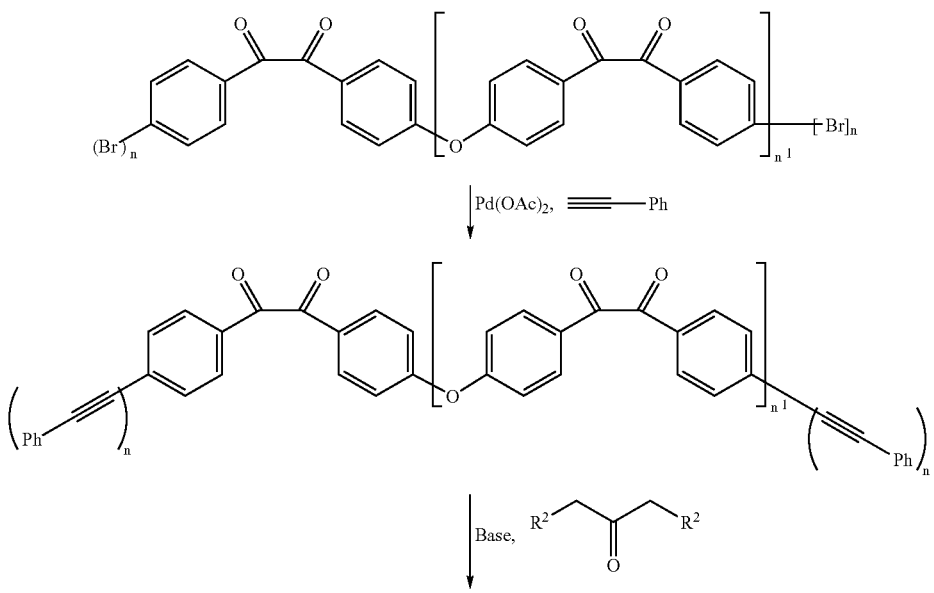

-continued
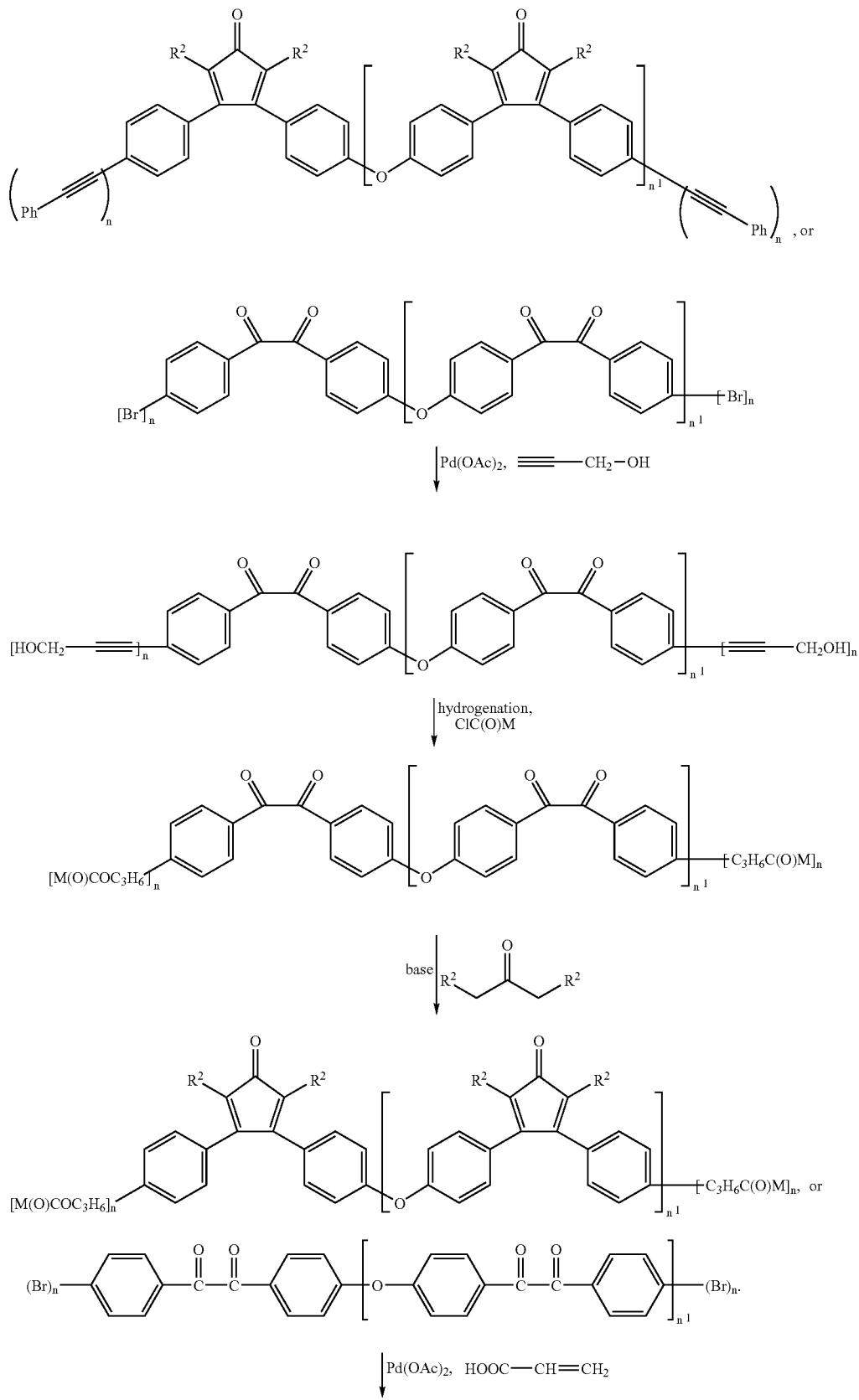

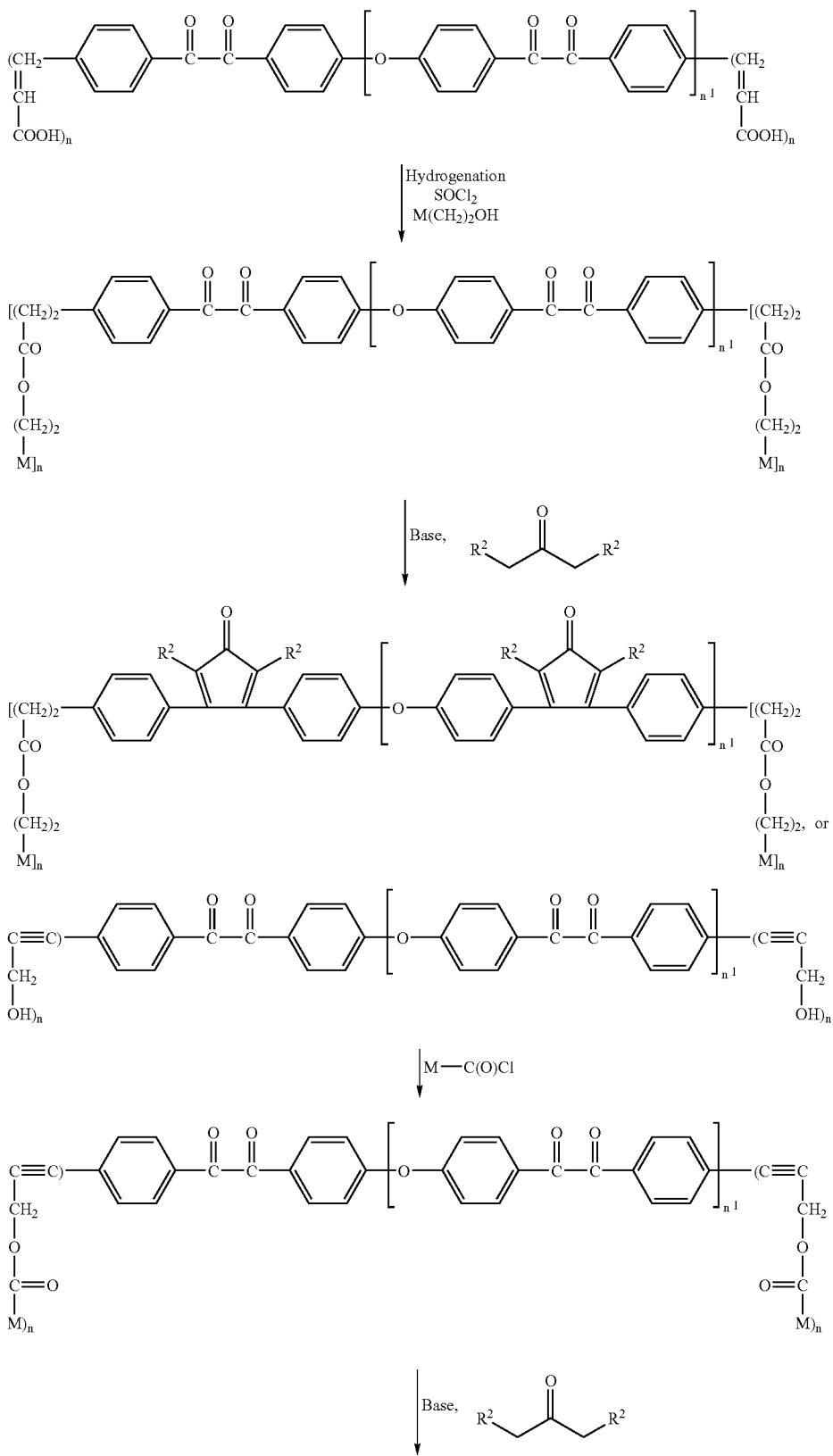

-continued
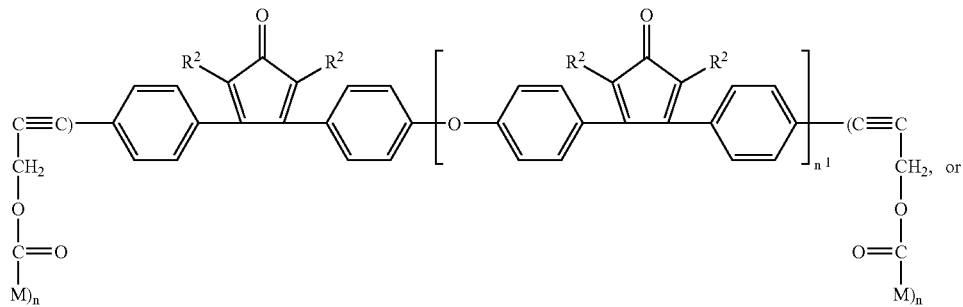
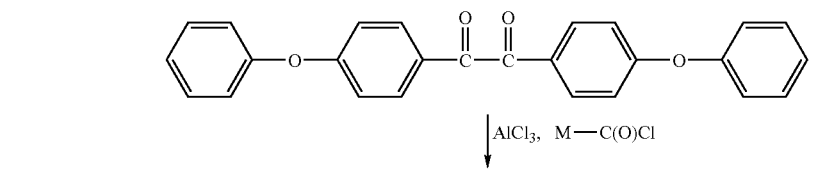
↓ AlCl₃, M—C(O)Cl
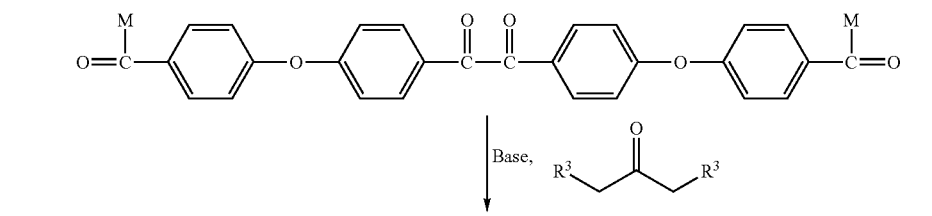
↓ Base, R³—C(O)—R³
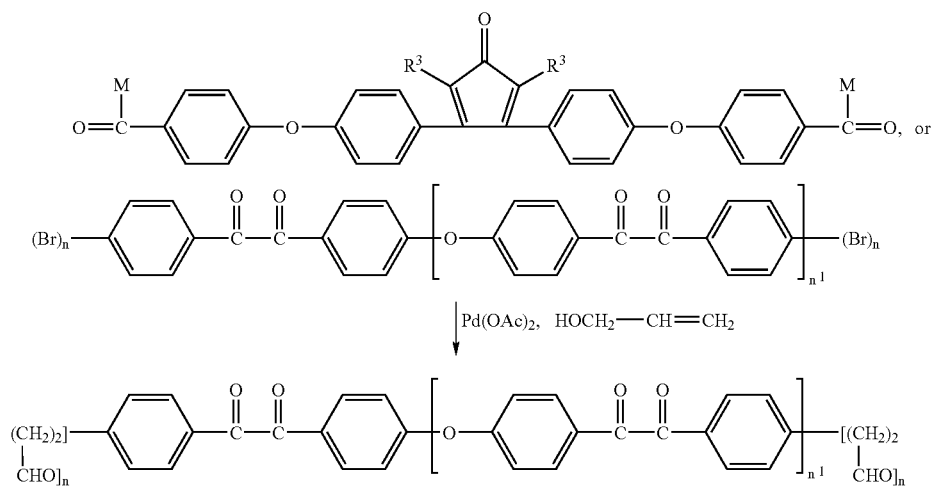
↓ Pd(OAc)₂, HOCH₂—CH=CH₂
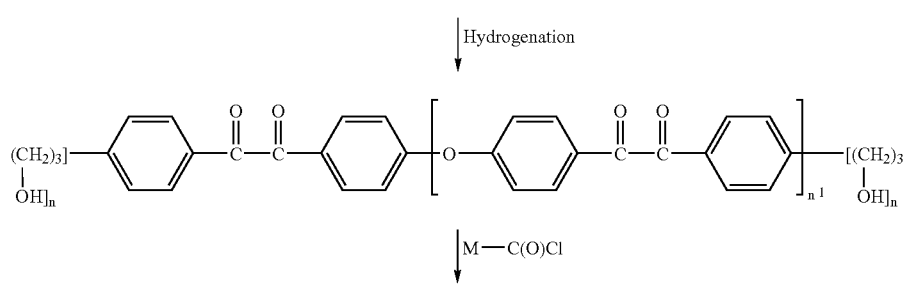
↓ Hydrogenation
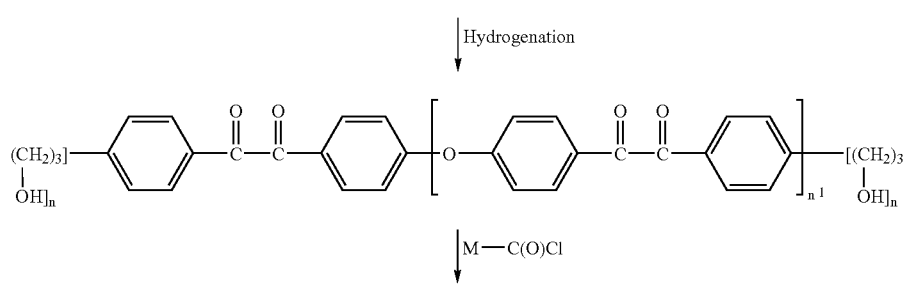
↓ M—C(O)Cl

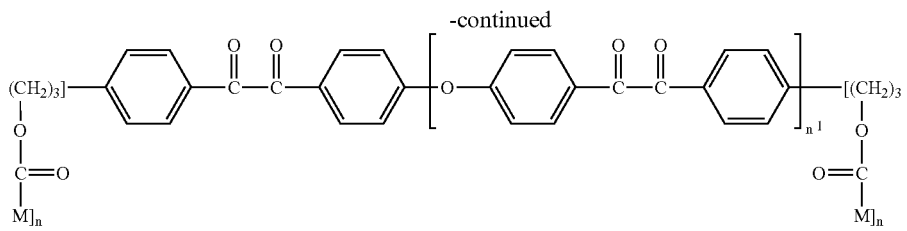

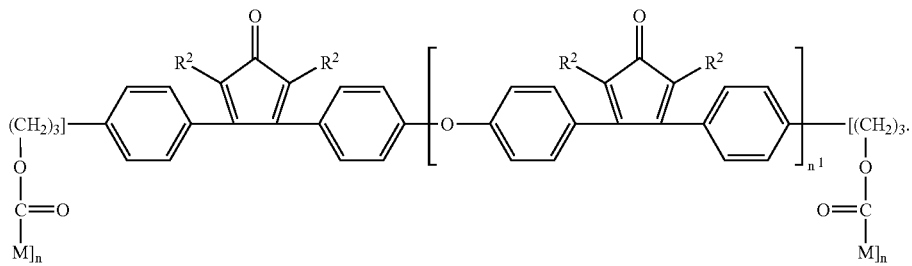

where $R^2$ and M are as previously defined;

$R^3$ is independently each occurrence is $C_{6-20}$ aryl-substituted ethynyl, -Z"-M, —C≡C-M, $C_{6-20}$ aryl, or inertly substituted aryl, with the proviso that in at least one occurrence $R^3$ is $C_{6-20}$ aryl-substituted ethynyl;

each n independently is 0, 1 or 2, with the proviso that in at least one occurrence n is 1 or 2; and $n^1$ is 0 or 1.

B-Staging of AxByMz Monomer

Preparation of oligomers and partially cross-linked polymers (b-staging) can be represented in one embodiment employing an $A_2B_2M_2$ monomer by the following illustration, where XL stands for a cross-lining polymer chain. A variety of similarly cross-linked polymers may be prepared by this technique.

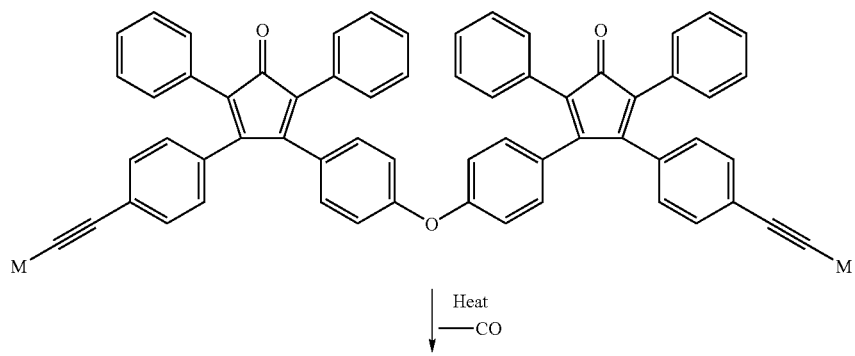

-continued

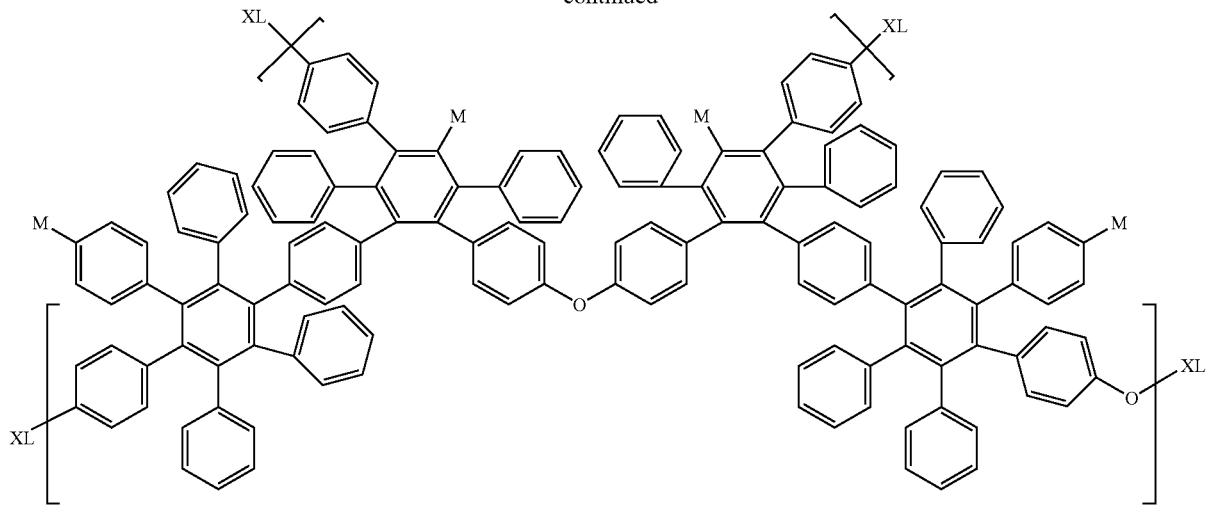

While not desiring to be bound by their belief, it is believed that polyphenylene oligomers and polymers are formed through a Diels-Alder reaction of the cyclopentadienone with the acetylene group when the mixture of monomer and optional solvent(s) is heated. The product may still contain quantities of cyclopentadienone and acetylene end groups. Upon further heating of the mixture or an article coated therewith, additional crosslinking can occur through the Diels-Alder reaction of the remaining cyclopentadienone or B groups with the remaining acetylene or A groups. Ideally, cyclopentadienone and acetylene groups are consumed at the same rate under Diels-Alder reaction conditions, preferably at temperatures from 280 to 350° C., more preferably from 285 to 320° C. For those monomers with a stoichiometric excess of A groups with respect to B groups, subsequent curing or vitrification may involve a similar cycloaddition or an addition reaction involving only said dienophilic functional groups.

The cross-linking reaction is preferably halted prior to the reaction of significant quantities of A and B functionality to avoid gel formation. The oligomer may then be applied to a suitable surface prior to further advancement or curing of the composition. While in an oligomerized or b-stage, the composition is readily applied to substrates by standard application techniques, and forms a level surface coating which covers (planerizes) components, objects or patterns on the surface of the substrate. Preferably, at least ten percent of the monomer remains unreacted when b-staged. Most preferably, at least twenty percent of the monomer remains unreacted. One may determine the percentage of unreacted monomer by visible spectra analysis or SEC analysis.

Suitable solvents for preparing coating compositions of b-staged compositions include mesitylene, methyl benzoate, ethyl benzoate, dibenzylether, diglyme, triglyme, diethylene glycol ether, diethylene glycol methyl ether, dipropylene glyco methyl ether, dipropylene glycol dimethyl ether, propylene glycol methyl ether, dipropylene glycol monomethyl ether acetate, propylene carbonate, diphenyl ether, gamma-butyrolactone. The preferred solvents are mesitylene, gamma-butyrolactone, diphenyl ether and mixture thereof.

Alternatively, the monomers can be polymerized in one or more solvents at elevated temperature and the resulting solution of oligomers can be cooled and formulated with one or more additional solvents to aid in processing. In another approach, the monomer can be polymerized in one or more solvents at elevated temperature to form oligomers which can be isolated by precipitation into a non-solvent. These isolated oligomers can then be redissolved in a suitable solvent for processing. Furthermore, through selective use of the precipitation method, separation of the oligomers into various molecular weight products is often possible.

The monomers of the present invention or b-staged oligomers thereof are suitably employed in a curable composition alone or as a mixture with other monomers containing two or more functional groups (or b-staged oligomers thereof) able to polymerize by means of a Diels-Alder or similar cycloaddition reaction. Examples of such other monomers include compounds having two or more cyclopentadienone functional groups and/or acetylene functional groups or mixtures thereof, such as those previously disclosed in U.S. Pat. Nos. 5,965,679 and 6,359,091. In the b-stage curing reaction, a dienophilic group reacts with the cyclic diene functionality, causing elimination of L and aromatic ring formation. Subsequent curing or vitrification may involve a similar cycloaddition or an addition reaction involving only the dienophilic functional groups.

Additional polymerizable monomers containing A and/or B functionality may be included in a curable composition according to the present invention. Examples include compounds of the formula:

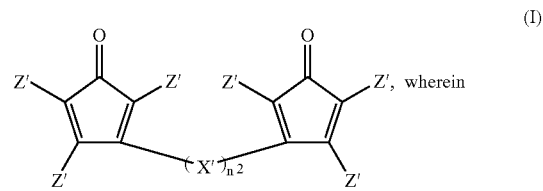

(I)

Z' is independently in each occurrence hydrogen, an unsubstituted or inertly substituted aromatic group, an unsubstituted or inertly substituted alkyl group, or —W—(C≡C-Q)$_q$;

X' is an unsubstituted or inertly substituted aromatic group, —W—C≡C—W—, or

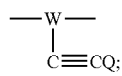

W is an unsubstituted or inertly substituted aromatic group, and

Q is hydrogen, an unsubstituted or inertly substituted $C_{6-20}$ aryl group, or an unsubstituted or inertly substituted $C_{1-20}$ alkyl group, provided that at least two of the X' and/or Z' groups comprise an acetylenic group, q is an integer from 1 to 3; and $n^2$ is an integer of from 1 to 10.

Examples of the foregoing polyfunctional monomers that may be used in conjunction with the monomers of the present invention include compounds of formulas II-XXV:

Formula II:

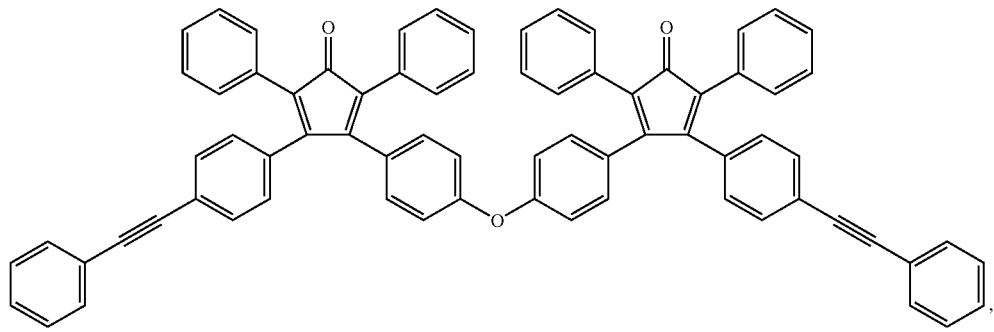

Formula III (a mixture of):

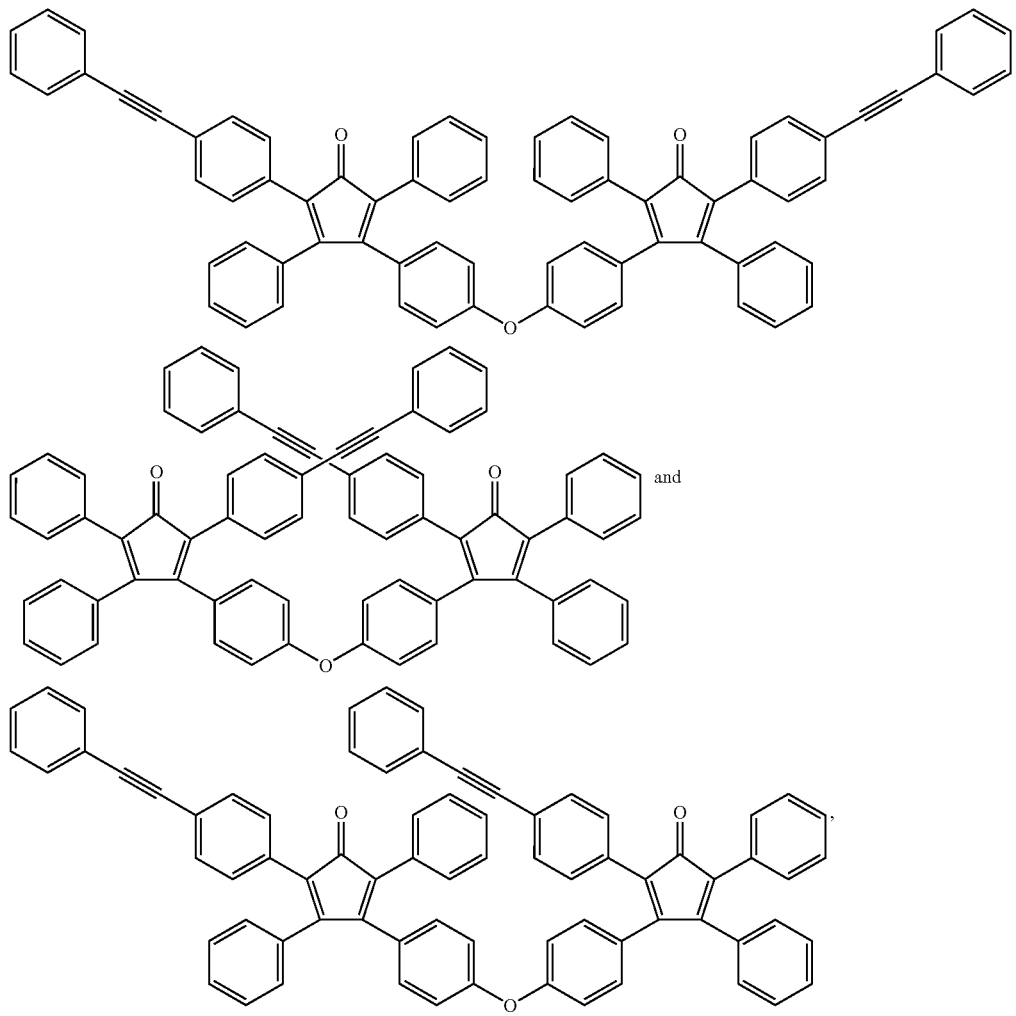

and

Formula IV:
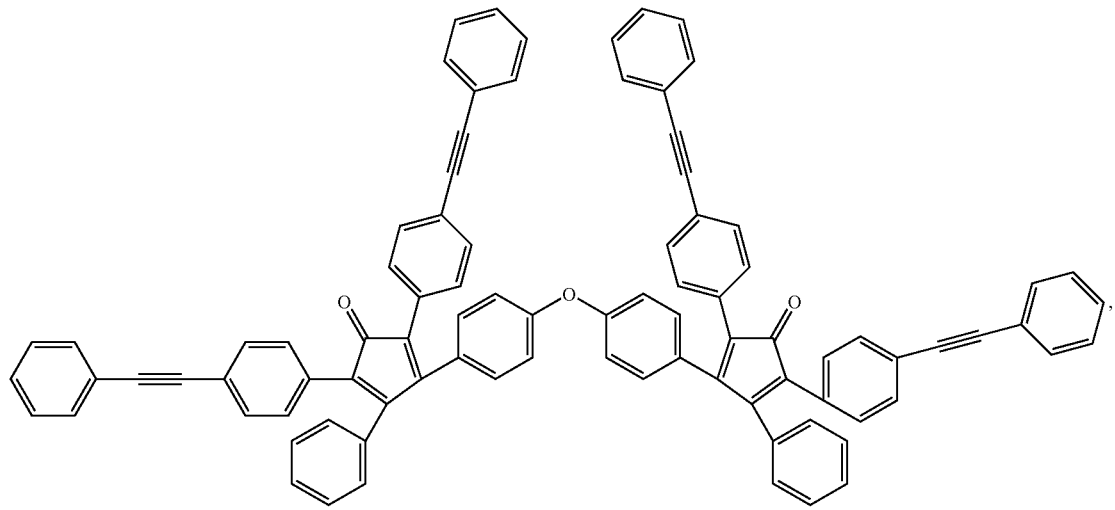
Formula V:
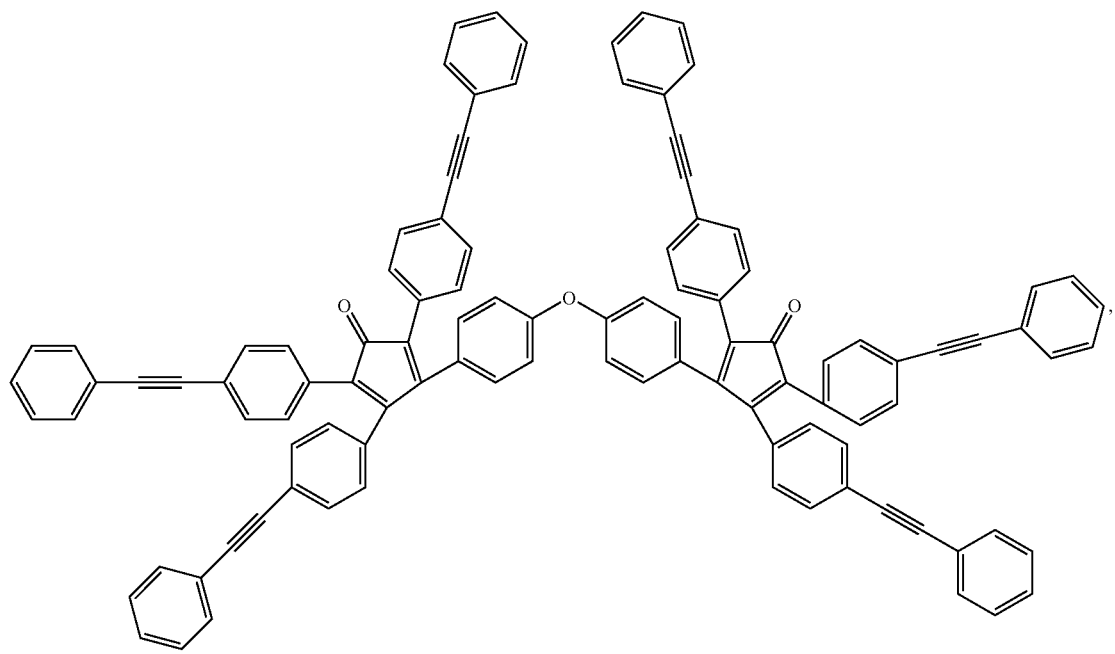
Formula VI:
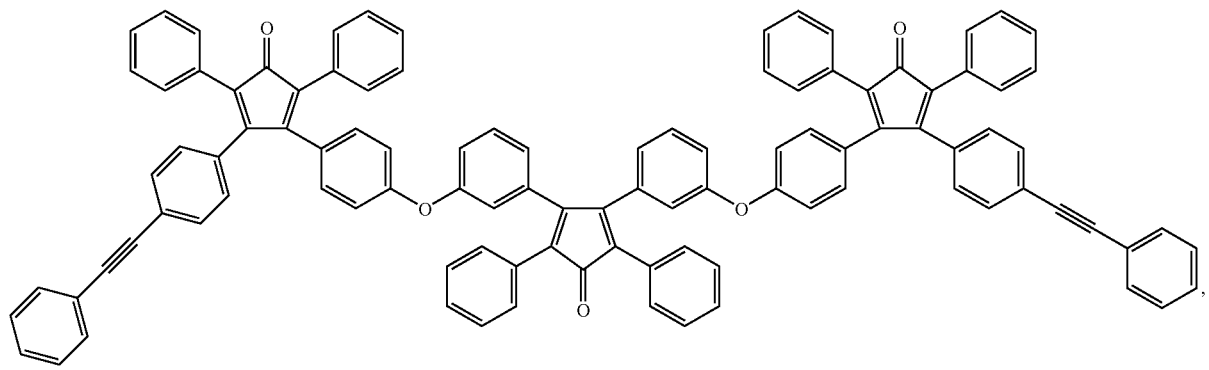

-continued
Formula VII:
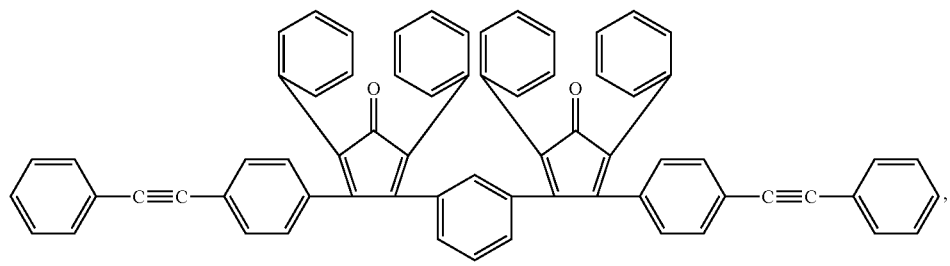
Formula VIII:
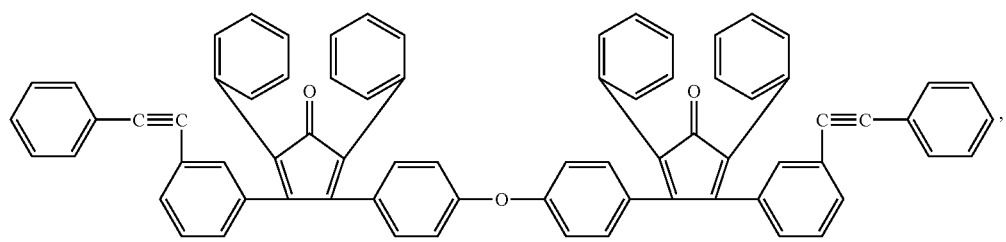
Formula IX:
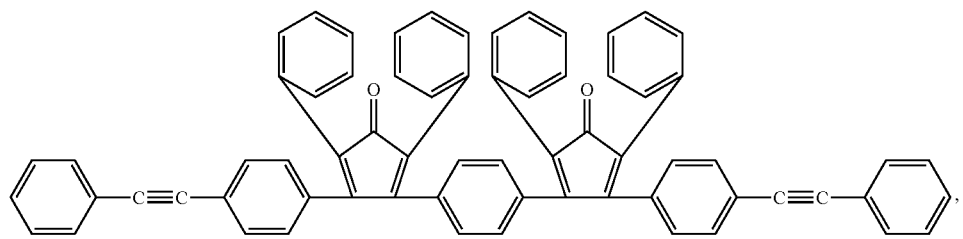
Formula X:
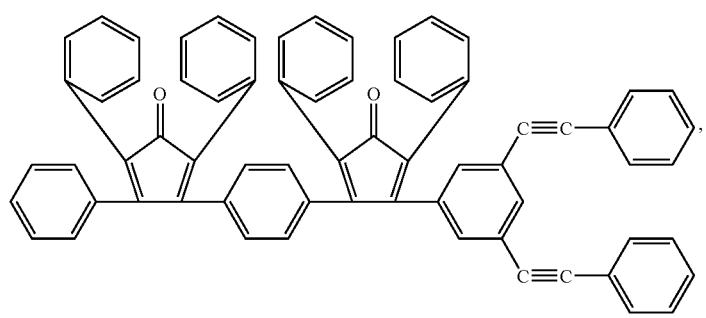
Formula XI:
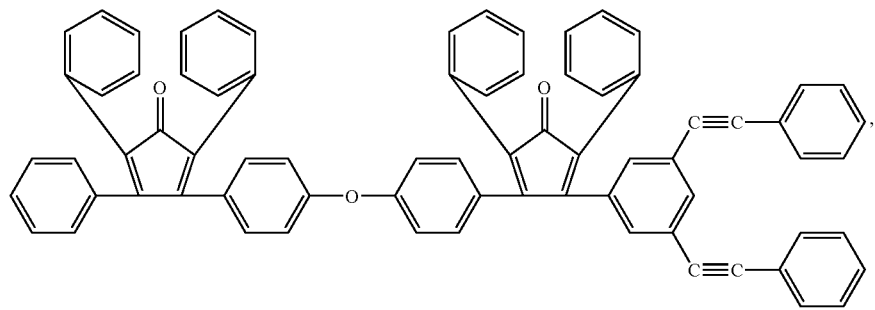

-continued
Formula XII:
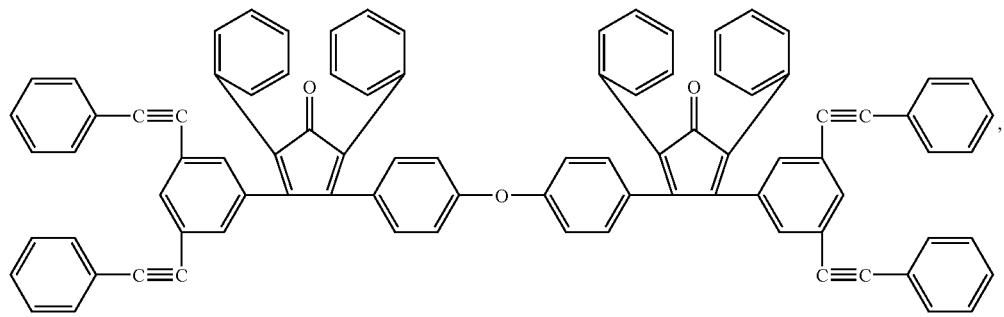
Formula XIII:
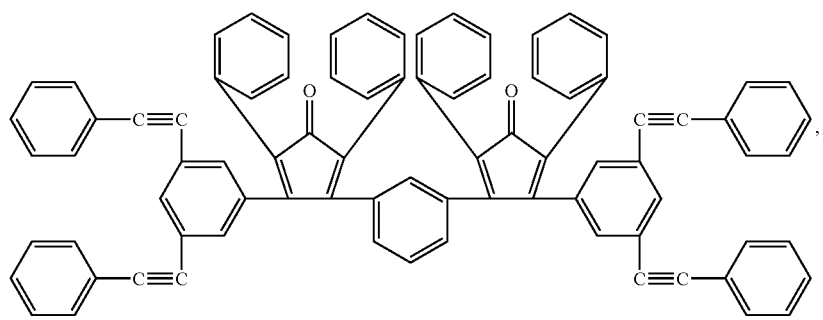
Formula XIV:
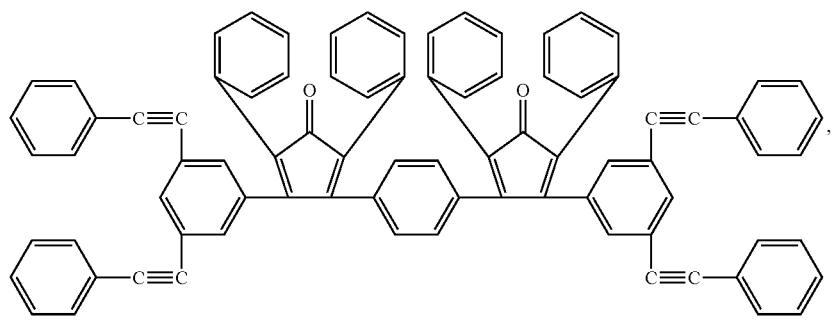
Formula XV:
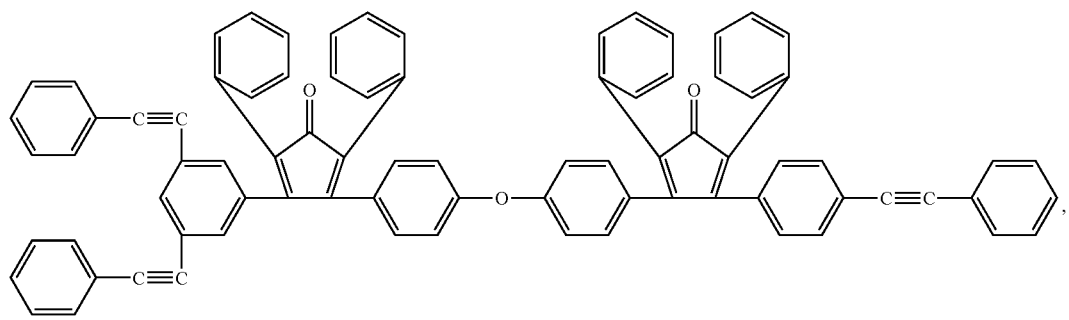

-continued
Formula XVI:
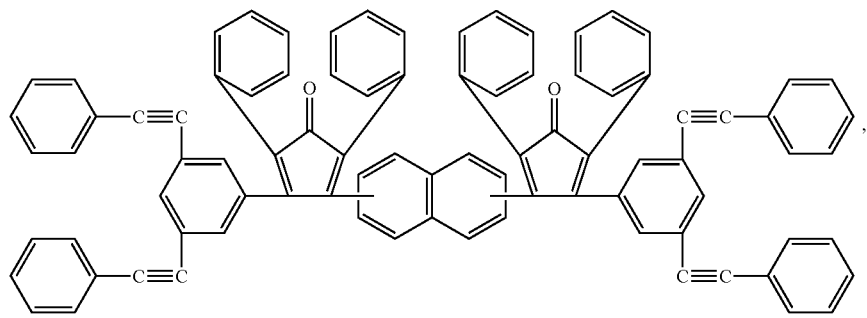
Formula XVII:
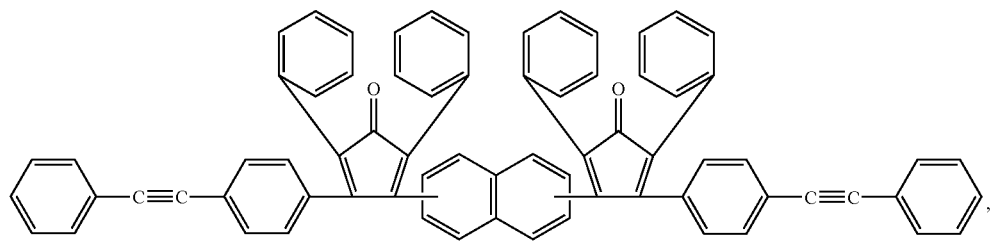
Formula XVIII:
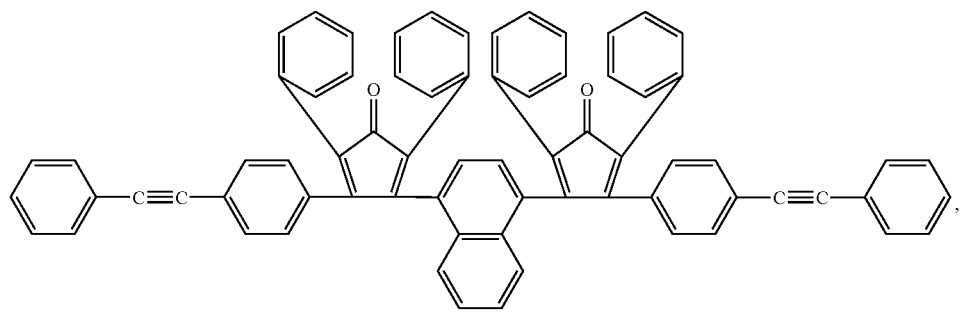
Formula XIX:
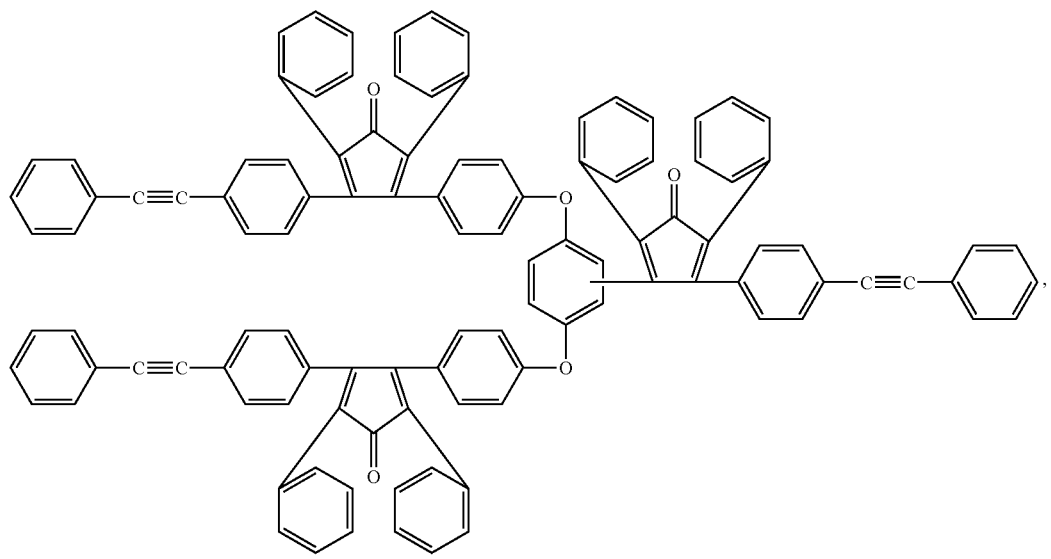

Formula XX (a mixture of):
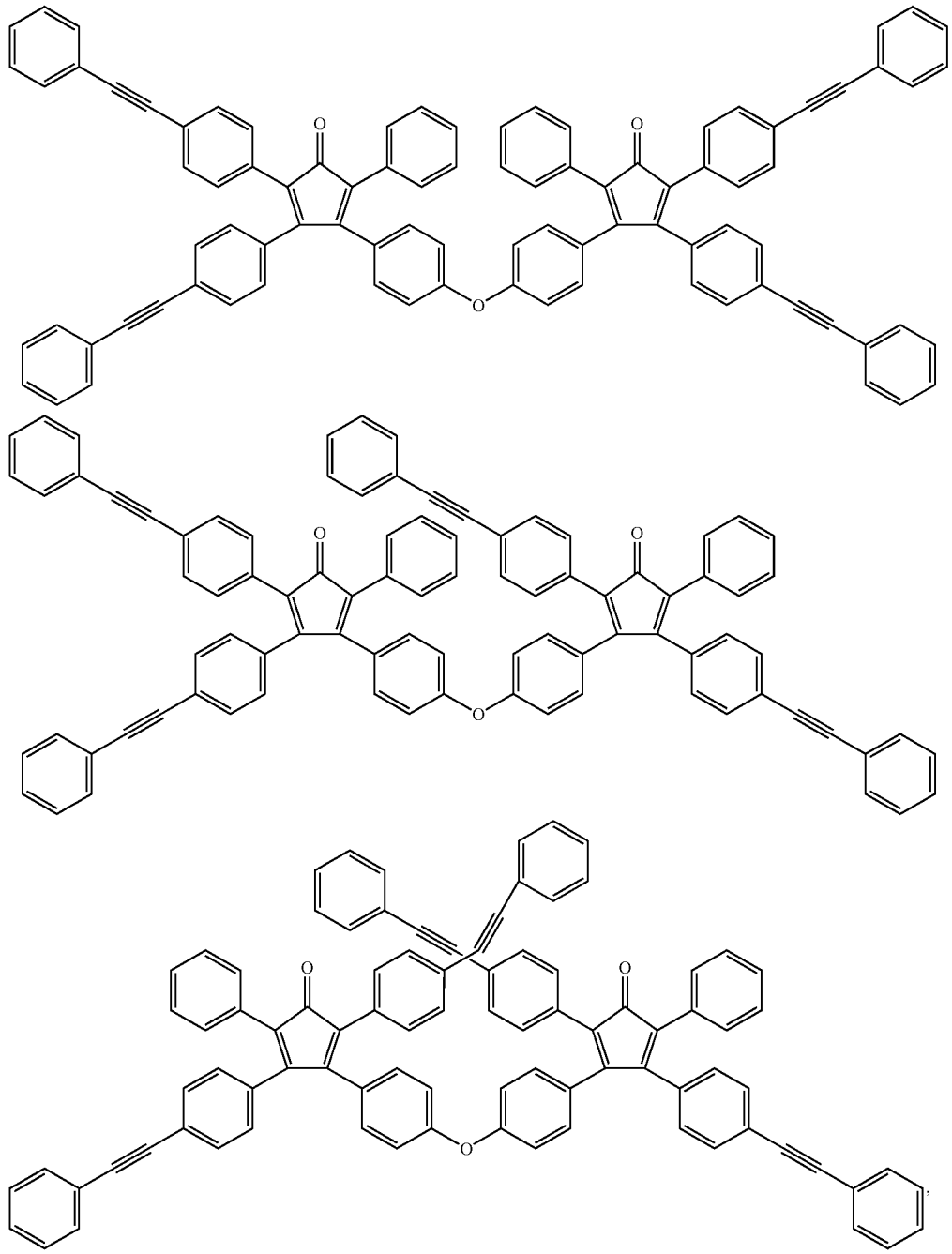
Formula XXI (a mixture of):
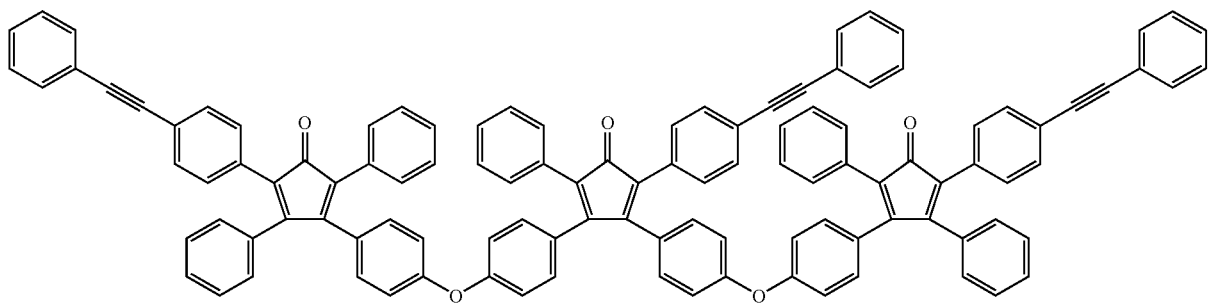

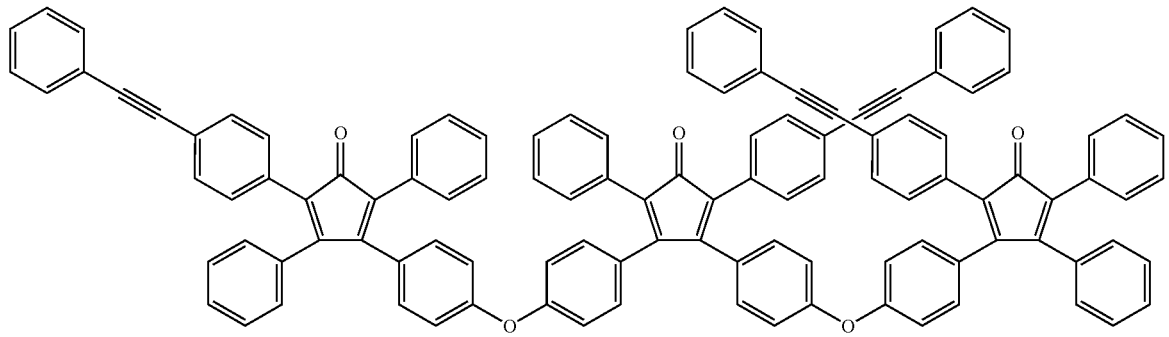
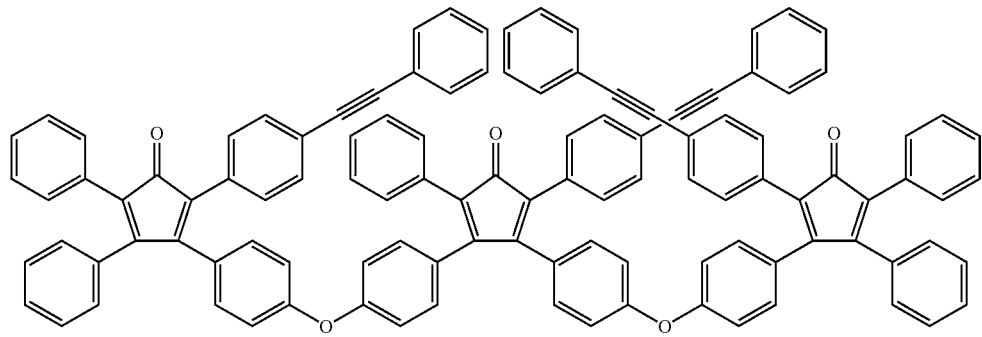
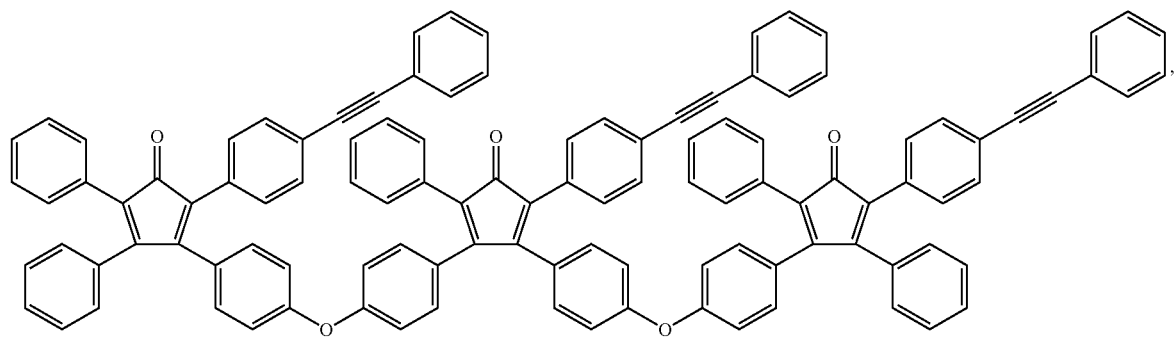
Formula XXII (a mixture of):
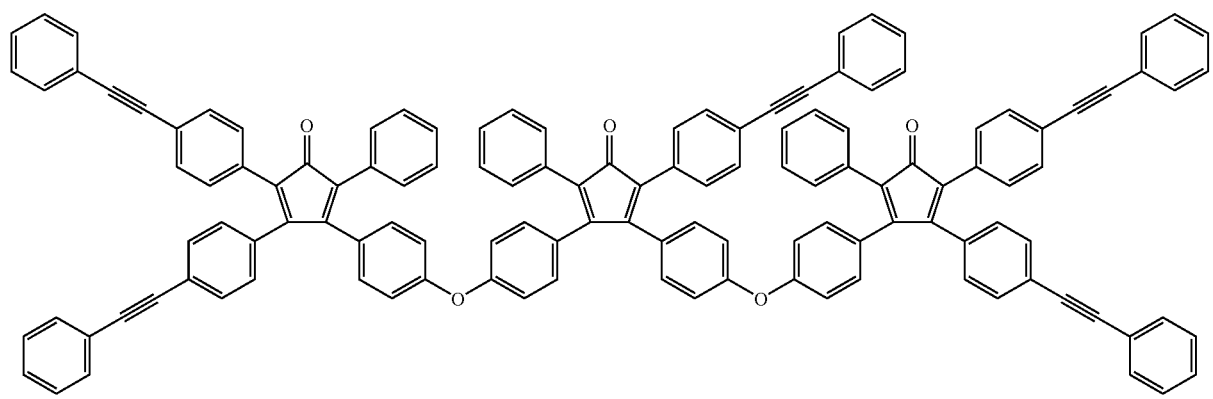

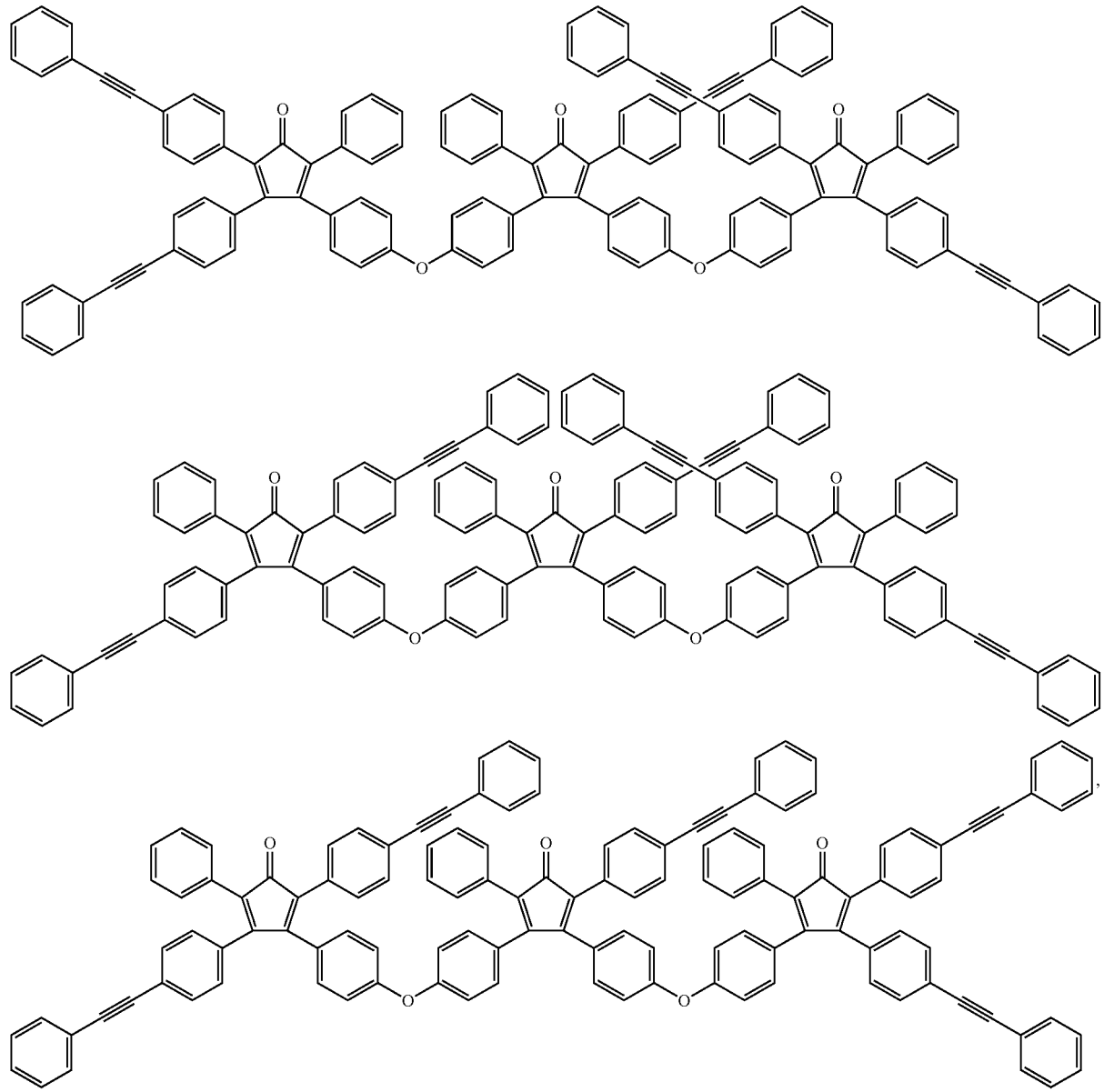
Formula XXIII:
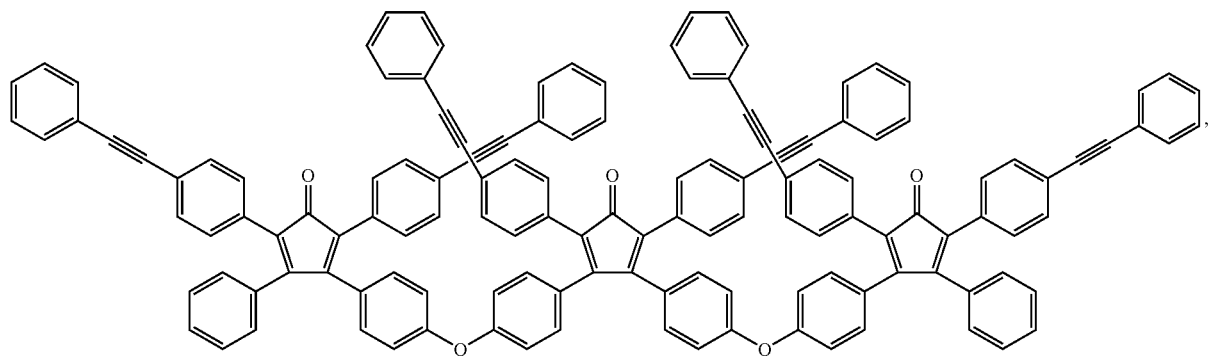

Formula XXIV:

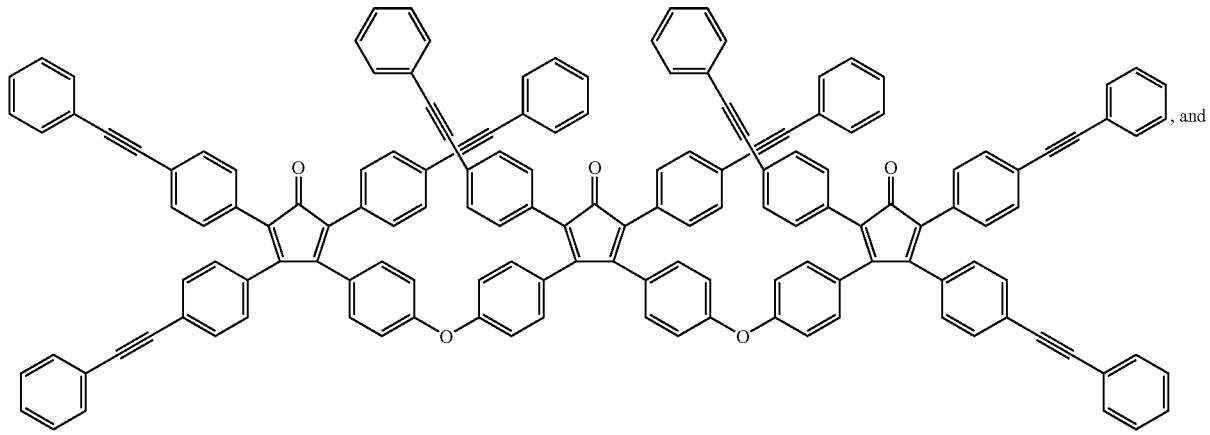

, and

Formula XXV:

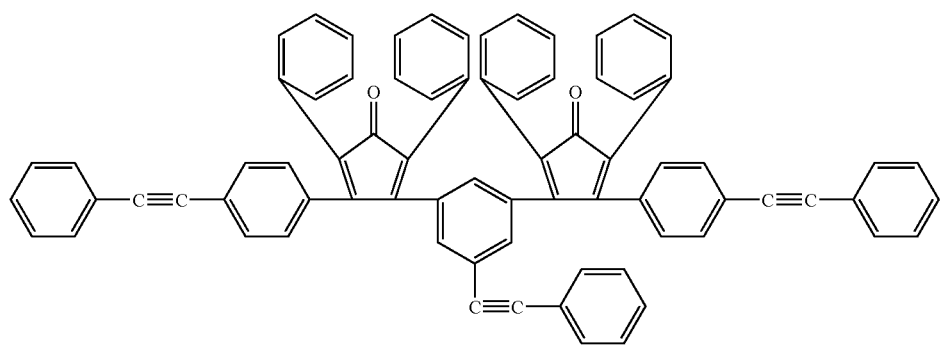

The foregoing monomers I-XXV where the ring structure is a cyclopentadienone may be made, for example, by condensation of substituted or unsubstituted benzils with substituted or unsubstituted benzyl ketones (or analogous reactions) using conventional methods such as those previously disclosed with respect to AxByMz monomers. Monomers having other structures may be prepared as follows: Pyrones can be prepared using conventional methods such as those shown in the following references and references cited therein: Braham et. al., *Macromolecules* (1978), 11, 343; Liu et. al., *J. Org. Chem.* (1996), 61, 6693-99; van Kerckhoven et. al., *Macromolecules* (1972), 5, 541; Schilling et. al. Macromolecules (1969), 2, 85; and Puetter et. al., *J. Prakt. Chem.* (1951), 149, 183. Furans can be prepared using conventional methods such as those shown in the following references and references cited therein: Feldman et. al., *Tetrahedron Lett.* (1992), 47, 7101, McDonald et. al., *J. Chem. Soc. Perkin Trans.* (1979), 1 1893. Pyrazines can be prepared using methods such as those shown in Turchi et. al., *Tetrahedron* (1998), 1809, and references cited therein.

In a preferred embodiment of the invention employing mixtures of the present monomers and other monomers as previously disclosed, it is desirable to maintain a ratio of the corresponding A-functionality and B-functionality in the mixture such that the ratio of B-functional groups to A-functional groups in the reaction mixture is in the range of 1:10 to 10:1, and most preferably from 2:1 to 1:8. Preferably, the composition additionally comprises a solvent and optionally may also comprise a poragen.

Suitable poragens that may be separately added to a composition herein or bonded to the monomer include any compound that can form small domains in a matrix formed from the monomers and which can be subsequently removed, for example by thermal decomposition. Preferred poragens are polymers including homopolymers and interpolymers of two or more monomers including graft copolymers, emulsion polymers, and block copolymers. Suitable thermoplastic materials include polystyrenes, polyacrylates, polymethacrylates, polybutadienes, polyisoprenes, polyphenylene oxides, polypropylene oxides, polyethylene oxides, poly(dimethylsiloxanes), polytetrahydrofurans, polyethylenes, polycyclohexylethylenes, polyethyloxazolines, polyvinylpyridines, polycaprolactones, polylactic acids, copolymers of the monomers used to make these materials, and mixtures of these materials. The thermoplastic materials may be linear, branched, hyperbranched, dendritic, or star-like in nature. The poragen may also be designed to react with the cross-linkable matrix precursor or oligomer during or subsequent to b-staging to form blocks or pendant substitution of the polymer chain. For example, thermoplastic polymers containing reactive groups such as vinyl, acrylate, methacrylate, allyl, vinyl ether, maleimido, styryl, acetylene, nitrile, furan, cyclopentadienone, perfluoroethylene, BCB, pyrone, propiolate, or orthlo-diacetylene groups can form chemical bonds with precursor compounds containing suitable reactive groups, such as bromo-, vinyl- or ethynyl functionality.

Suitable block copolymer poragens include those wherein one of the blocks is compatible with cross-inked polymer matrix resin and the other block is incompatible therewith. Useful polymer blocks can include polystyrenes such as polystyrene and poly-α-methylstyrene, polyacrylonitriles, polyethylene oxides, polypropylene oxides, polyethylenes, polylactic acids, polysiloxanes, polycaprolactones, polyurethanes, polymethacrylates, polyacrylates, polybutadienes, polyisoprenes, polyvinyl chlorides, and polyacetals, and amine-capped alkylene oxides (commercially available as Jeffamine™ polyether amines from Huntsman Corp.).

Highly preferred poragens are crosslinked polymers made by solution or emulsion polymerization. Such polymerization techniques are known in the art, for example, EP-A-1,245, 586, and elsewhere. Very small crosslinked hydrocarbon based polymer particles have been prepared in an emulsion polymerization by use of one or more anionic-, cationic-, or non-ionic surfactants. Examples of such preparations may be found in *J. Dispersion Sci. and Tech.*, vol. 22, No. 2-3, 231-244 (2001); "The Applications of Synthetic Resin Emulsions", H. Warson, Ernest Benn Ltd., 1972, p. 88; *Colloid Polym. Sci.*, 269, 1171-1183 (1991), *Polymer. Bull.*, 43, 417-424 (1999), PCT 03/04668, filed Feb. 12, 2003 and U.S. Ser. No. 10/366,494, filed Feb. 12, 2003, among other sources.

Preferably, the monomer is chemically bound or grafted to the poragen by a palladium catalyzed reaction of an ethynyl terminated poragen precursor with an aromatic halogen containing diketone or diaryl-substituted acetone derivative. This may be best accomplished by incorporating the functionalized poragen in the monomer prior to b-staging. In this manner, the bound poragen is uniformly incorporated into the resulting cured polymer. The mixture is then coated onto a substrate (preferably solvent coated as for example by spin coating or other known methods). The matrix is cured and the bound poragen is removed, prior to, simultaneously with, or after removal of the poragen formed from the bound mesogenic poragen forming moiety. In a preferred embodiment both poragens are removed by heating to a temperature above the thermal decomposition temperature of the poragen. The process results in uniform, extremely small poragens in the resin, and, if removed, uniform, extremely small pores (nanopores) in the vitrified resin matrix. Porous films prepared in this manner are useful in making integrated circuit articles where the film separates and electrically insulates conductive metal lines from each other.

Porous Matrix from AxBvMz Monomers and Oligomers

The self-assembled poragen formed from the mesogenic poragen forming moieties is desirably a material that, upon removal, results in formation of voids or pores in the matrix having an average pore diameter from 1 to 200 nm, more preferably from 2 to 100 nm, most preferably from 5 to 50 nm. Desirably, the pores are not interconnected, that is the resulting matrix has a closed cell structure. The nature of the bound mesogenic poragen is chosen based on a number of factors, including the size and shape of the pore to be generated, the method of poragen decomposition, the level of any poragen residue permitted in the porous nanostructure, and the reactivity or toxicity of any decomposition products formed. It is also important that the matrix have enough crosslinking density to support the resulting porous structure. Discotic mesogenic poragen forming moieties that are capable of formation of unique shaped voids such as polygonal, especially hexagonal, or rod-shaped moieties capable of forming pores of approximately circular cross-section may be employed.

In particular, the temperature at which pore formation occurs should be carefully chosen to be sufficiently high to permit prior solvent removal and at least partial vitrification of the b-staged oligomer, but below the glass temperature, Tg, of the vitrified matrix. If pore formation takes place at a temperature at or above the Tg of the matrix, partial or full collapse of the pore structure may result.

According to one method of preparing the monomers of the invention, 1,3-bis(4-bromophenyl)-2-propanone is (1) difunctionalized via a modified Heck reaction (palladium catalyzed coupling), (2) selectively hydrogenated (3) further difunctionalized with mesogenic poragen forming moieties and then (4) condensed with 4,4'-bis[(4-phenylethynylphenyl)-glyoxalyl]phenyl ether according to the following synthetic scheme:

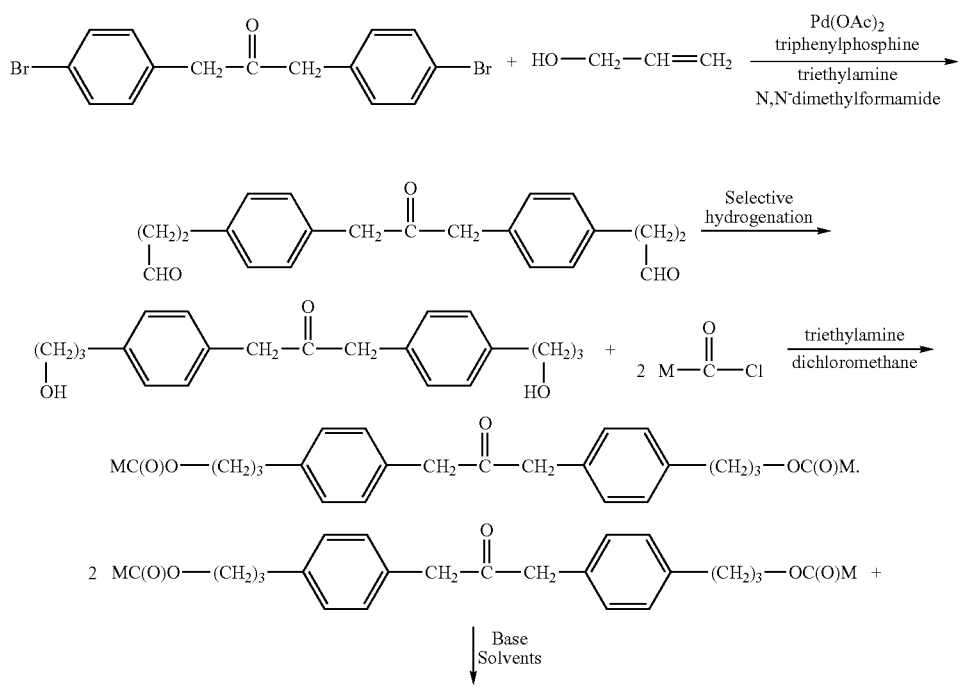

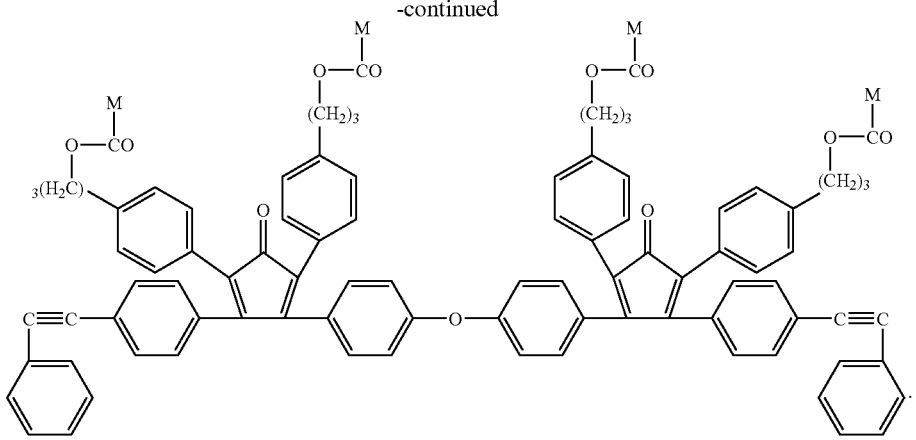

Alternatively, the mesogenic poragen forming moiety can be bound by reaction of reactive functionality, especially ethylenic unsaturation in a monomer precursor, with an addition polymerizable monomer or telegen. An example is the reaction of a vinyl capped polystyrene or a vinyl capped styrene oligomer with the benzocyclobutane functionalized monomer to make a block structure as shown in following scheme where m is an integer greater than or equal to one, and M is the mesogenic poragen forming moiety:

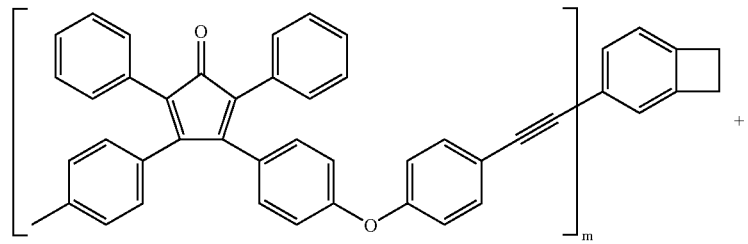

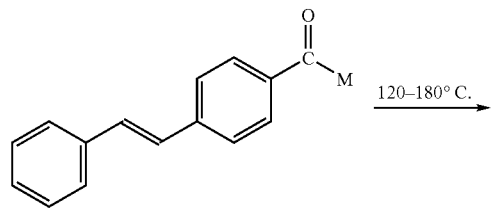

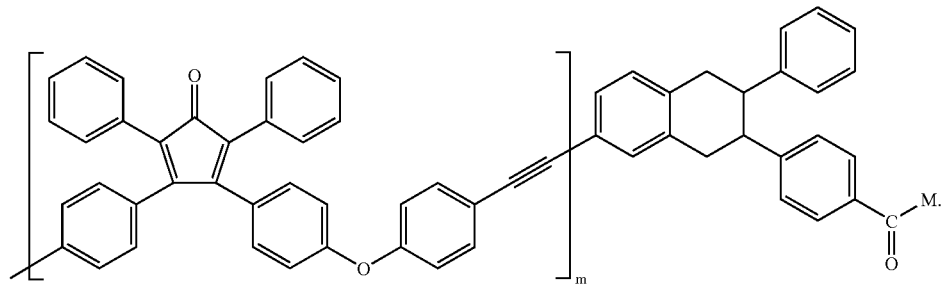

Using different monomer precursors, block copolymer or random copolymers with a variety of architectures can be prepared. One reaction scheme is depicted as follows, where m and $n^3$ are integers greater than or equal to one:

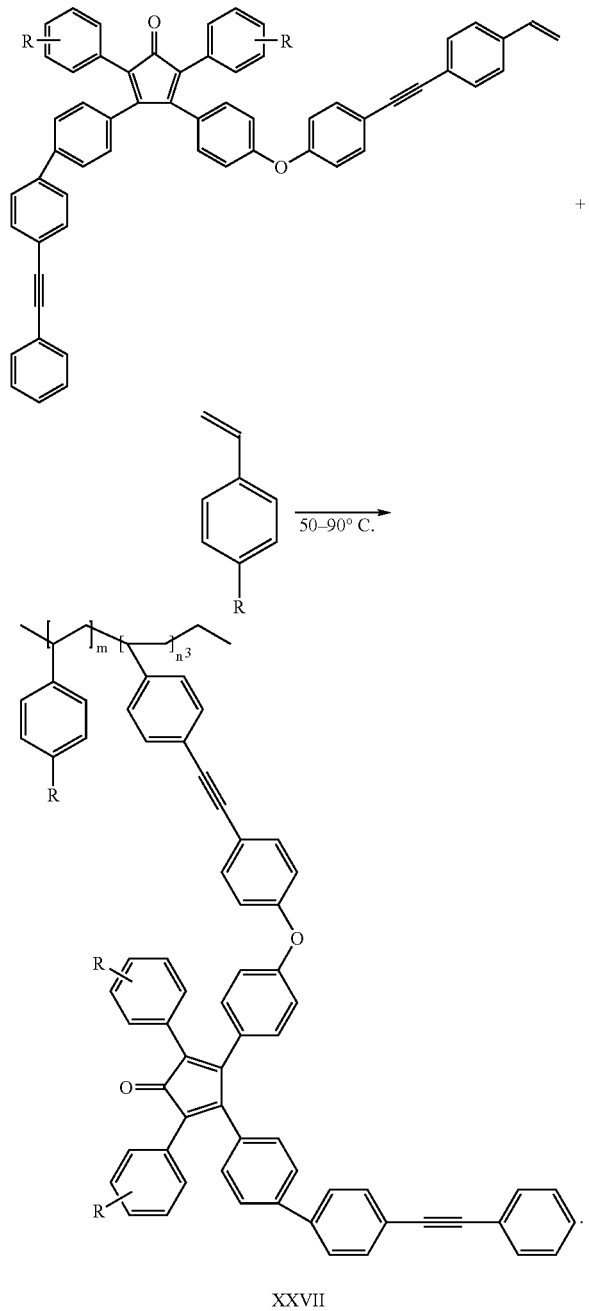

XXVII

R = H, halo, $C_{1-4}$ alkyl, M C(O)M, etc.

The result of incorporating mesogenic poragen forming moieties into the matrix during its formation in the foregoing manners is a near uniform correspondence of pores with initial mesogenic poragen forming moieties and limited or no agglomeration and heterogeneous phase separation of the poragens. In addition, separate thermal processing for purposes of pore formation may be avoided if the decomposition temperature of the resulting mesogenic poragen is appropriately chosen. The resultant articles, including films or coatings, are extremely low dielectric constant, nanoporous materials having highly uniform electrical properties due to the uniformity of pore distribution.

Highly desirably, the matrix materials formed from monomers of the present invention are relatively thermally stable at temperatures of at least 300° C., preferably at least 350° C. and most preferably at least 400° C. In addition, the matrix polymer also has a Tg of greater than 300° C. and more preferably greater than 350° C. after being fully crosslinked or cured. Further desirably, the crosslinking or vitrification temperature of the invention, defined as the temperature upon heating at which flexural modulus increases most quickly, is desirably below the decomposition temperature of the resulting poragen, preferably less than or equal to 400° C., most preferably, less than or equal to 300° C. This property allows crosslinking to take place before substantial pore formation occurs, thereby preventing collapse of the resulting porous structure. Finally, in a desirable embodiment of the invention, the flexural modulus of the partially crosslinked and cured polymer, either with or without poragen present, desirably reaches a maximum at temperatures less than or equal to 400° C., preferably less than or equal to 350° C., and most preferably, less than or equal to 300° C. and little or no flexural modulus loss occurs upon heating the fully cured matrix to a temperature above 300° C., such as may be encountered during pore formation via thermolysis.

In one suitable method of operation, monomer, optional poragen, optional mesogenic substances, and optional solvent are combined and heated at elevated temperature, preferably at least 160° C., more preferably at least 200° C. for at least several hours, more preferably at least 24 hours to make a solution of crosslinkable b-staged oligomers bearing mesogenic poragens formed by self-assembly of the various mesogenic poragen forming moieties. The amount of monomer relative to the amount of separately added poragen or optional mesogenic substances, may be adjusted to give a cured matrix having the desired porosity. Alternatively, a comonomer with or without chemically bonded mesogenic poragen forming moieties may be included in the polymerizable composition to control the quantity of pores in the resulting matrix. Preferably, the amount of mesogenic poragen forming moiety based on total monomer weight is from 5 to 80 percent, more preferably from 20 to 70 percent, and most preferably from 30 to 60 percent.

Solutions containing monomers comprising mesogenic poragen forming moieties for use herein desirably are sufficiently dilute to result in optically clear solutions having the desired coating and application properties. Preferably, the amount of solvent employed is in the range of 50-95 percent based on total solution weight. The solution may be applied to a substrate by any suitable method such as spin coating, and then heated to remove most of the remaining solvent and leave the monomer or b-staged oligomer, containing self-assembled poragen moieties dispersed therein. During the solvent removal process and/or during subsequent thermal processing, the poragen phase desirably forms separate uniformly dispersed. occlusions in a fully cured or cross-linked matrix. Upon continued or subsequent heating, the occlusions decompose into decomposition products that may diffuse through the cured matrix, thereby forming a porous matrix.

The concentration of pores in the above porous matrix is sufficiently high to lower the dielectric constant or refractive index of the cured polymer, but sufficiently low to allow the resulting porous matrix to withstand the process steps required in the fabrication of microelectronic devices. Preferably, the quantity of pores in the resulting cross-linked porous matrix is sufficient to result in materials having a dielectric constant of less than 2.5, more preferably less than 2.0.

The average diameter of the pore is preferably less than 100 nm, more preferably less than 20 nm, and most preferably less than 10 nm. The pore sizes can be easily controlled by adjusting the size of the mesogenic poragen forming moieties employed in preparing the monomers of the invention.

The compositions of the invention may be used to make dielectric films and interlayer dielectrics for integrated circuits in accordance with known processes, such as those of U.S. Pat. No. 5,965,679. To make a porous film the bound mesogenic poragen is preferably removed by thermal decomposition.

It is expressly intended that the foregoing disclosures of preferred, more preferred, highly preferred, or most preferred substituents, ranges, components or combinations with respect to any one of the embodiments of the invention is applicable as well to any other of the preceding or succeeding embodiments independently of the identity of any other specific substituent, range, component, or combination.

The invention is further illustrated by the following Examples that should not be regarded as limiting of the present invention. Unless stated to the contrary, implicit in the disclosure or conventional in the art, all parts and percents are based on weight. The present invention is operable in the absence of any undisclosed component, step or condition.

EXAMPLE 1

Synthesis of $A_4B_2M_2$ Monomer Containing Calix[4] arene Discotic Mesogens

A) Synthesis of 5,11,17,23-Tetrapropyl-25,26,27,28-tetrahydrocalix[4]arene 5,11,17,23-Tetraallyl-25,26,27,28-tetrahydroxycalix[4]arene is prepared using the method of Gutsche and Levine, *Journal of the American Chemical Society*, 104, 2652-2653 (1982). The 5,11,17,23-tetraallyl-25,26,27,28-tetrahydroxycalix[4]arene (0.05 allyl equivalent) and ethyl acetate (250 milliliters) are added to a 400 milliliter heavy walled glass bottle and then sparged with nitrogen. After removal of the air by nitrogen sparging, Raney nickel catalyst (5.0 gram of a 50 percent slurry in water at pH 10 washed once with deionized water) is added to the bottle which is stoppered and multiply purged with hydrogen to displace the nitrogen atmosphere. The bottle is then placed on a shaking type agitator and pressurized to 450 kPa (50 psig) with hydrogen. Shaking of the pressurized bottle at room temperature commences and consumption of hydrogen is observed with intermittent recharging with hydrogen to the initial 450 kPa After no further hydrogen uptake occurs, the reaction slurry is recovered and filtered to remove the Raney nickel. The 5,11,17,23-tetrapropyl-25,26,27,28-tetrahydrocalix[4]arene is recovered as a solid product via rotary evaporation to remove solvent.

B) Synthesis of 5,11,17,23-Tetrapropyl-25,26,27-trimethoxy-28-hydroxycalix[4]arene 5,11,17,23-Tetrapropyl-25,26,27,28-tetrahydroxycalix[4]arene (0.0107 hydroxyl equivalent) is dissolved in N,N-dimethylformamide (35 milliliters). The resultant solution is then treated with BaO (1.81 grams), $Ba(OM_2(8H_2O)$ (1.94 grams) and dimethylsulfate (0.053 mole) The mixture is stirred 15 hours at room temperature followed by the addition of concentrated ammonium hydroxide (5 milliliters), then deionized water (35 milliliters). The product is extracted into chloroform, then washed with deionized water, dried over anhydrous sodium sulfate and then filtered through a medium fritted glass funnel. Rotary evaporation of the filtrate provides a solid, which is recrystallized from chloroform plus methanol. The crystalline product is recovered via filtration, then dried at 80° C. in the vacuum oven to a constant weight of 5,11,17,23-tetrapropyl-25,26,27-trimethoxy-28-hydroxycalix[4]arene.

C) Synthesis of 5,11,17,23-Tetrapropyl-25,26,27-trimethoxy-28-(2-hydroxyethyloxy)calix[4]arene 5,11,17,23-Tetrapropyl-25,26,27-trimethoxy-28-hydroxycalix[4]arene (0.005 mole), ethylene carbonate (0.0055 mole), 4-(N,N'-dimethylamino)pyridine (0.10 percent of total reactants) and triethylamine (1.0 percent of total reactants) are combined together with heating and stirring under a nitrogen atmosphere. Once a temperature of 140° C. is achieved, the course of the reaction is monitored via high pressure liquid chromatography (HPLC). Once full conversion of the phenolic hydroxyl group to the 2-hydroxyethyloxy group is achieved, the product is diluted with toluene (55 milliliters) and heated to provide a solution which is then allowed to slowly cool to room temperature to provide crystalline product. The crystalline product is recovered via filtration, then recrystallized from sufficient boiling acetonitrile to form a solution. The recrystallized product recovered via filtration is dried at 80° C. in the vacuum oven to a constant weight of 5,11,17,23-tetrapropyl-25,26,27-trimethoxy-28-(2-hydroxyethyloxy)calix[4]arene:

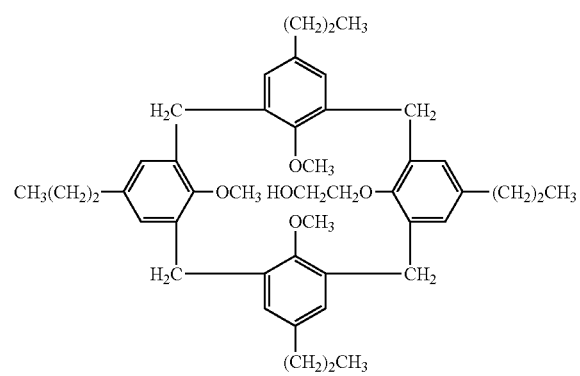

D) Synthesis of 4-Bromophenylacetyl Chloride

4-Bromophenylacetic acid (99.5 grams, 0.46 mole) and N,N-imethylformamide (2 milliliters) are added under a dry nitrogen atmosphere to a predried one liter glass single neck round bottom Schlenk reactor containing a predried magnetic stirring bar. After sealing under dry nitrogen, the reactor is placed on a Schlenk line under slightly positive nitrogen pressure. Thionyl chloride (300 milliliters) is added under a dry nitrogen atmosphere to a predried glass addition funnel which is outfitted with a Schlenk adapter, then sealed under dry nitrogen and placed on the Schlenk line. The reactor and addition funnel are coupled under dynamic nitrogen flow, after which the thionyl chloride is added dropwise to the stirred reactor. Nitrogen flow is maintained into the Schlenk reactor, while gas from the reaction is vented through the Schlenk adapter on the addition funnel and into a scrubber system. At the completion of the thionyl chloride addition, the addition funnel is replaced under dynamic nitrogen flow with a condenser capped with a Schlenk adapter vented into the scrubber system, then a thermostatically controlled heating mantle is used to gently heat the reactor contents to 60° C. After holding for 2.5 hours at 60° C., the excess thionyl chloride is stripped from the product by applying vacuum from the Schlenk manifold. The resulting 4-bromophenylacetyl chloride product (106 grams, 98.1 percent isolated yield) is maintained under dry nitrogen until use.

E) Synthesis of
4,4'-bis[(4-Bromophenyl)acetyl]phenyl ether

Diphenyl ether (200.96 grams, 1.1805 moles), aluminum chloride (321.15 grams, 2.409 moles) and anhydrous 1,2-dichloroethane (2.1 liters) are added under a dry nitrogen atmosphere to a predried five liter glass three neck round bottom reactor containing a predried magnetic stirring bar. After sealing under dry nitrogen, the reactor is placed on a Schlenk line under slightly positive nitrogen pressure. An ice and salt bath is then placed under the reactor 25 minutes before starting the reaction. 4-Bromophenylacetyl chloride (556.26 grams, 2.361 moles) is added under a dry nitrogen atmosphere to a predried glass addition funnel which is outfitted with a Schlenk adaptor, then sealed under dry nitrogen and placed on the Schlenk line. The reactor and addition funnel are coupled under dynamic nitrogen flow, then the 4-bromophenylacetyl chloride solution is added dropwise to the stirred reactor over a 3.7 hour period. After 2 hours of post reaction, magnetic stirring is shut off, the center port of the reactor is opened and a glass stirring shaft with polytetrafluoroethylene paddles is inserted then coupled to a variable speed motor to provide mechanical stirring of the reactor contents. A second port is opened and outfitted with an addition funnel containing chilled deionized water. Dropwise addition of chilled deionized water commences simultaneous with mechanical stirring, inducing a massive precipitation of light yellow colored product after addition of the first few drops of water. Water addition continues until all orange red color is gone with a stirred slurry of white solid in a purple colored liquid remaining. The stirred slurry is maintained until cooling to 23° C. has occurred, at which time, filtration through a coarse fritted glass funnel commences. After washing the packed bed of white powder on the filter with deionized water, it is removed, divided into 6 approximately equal portions, then washed in a blender with 250 milliliters of deionized water per portion. The washed product is recovered via filtration on a medium fritted glass funnel followed by drying in the vacuum oven at 80° C. to provide 498.3 grams (74.8 percent isolated yield) of 4,4'-bis[(4-bromophenyl) acetyl]phenyl ether. HPLC analysis reveals the presence of the desired product at 100 area percent.

F) Synthesis of
4,4'-bis[(4-Bromophenyl)glyoxalyl]phenyl ether 4,4'-bis[(4-Bromophenyl)acetyl]phenyl ether (212.48 grams, 0.3766 mole) and dimethylsulfoxide (3.1 liters) are added to a five liter glass three neck round bottom reactor outfitted with a glass mechanical stirring rod with polytetrafluoroethylene paddles. The reactor is additionally outfitted with a condenser (not chilled) vented into a scrubber system and a thermometer. Aqueous 48 percent hydrobromic acid (444.4 grams) is added dropwise over a 32 minute period to the stirred slurry in the reactor, inducing an exotherm to 39° C. A thermostatically controlled heating mantle is placed under the reactor and gentle heating over a 3.2 hour period to 100° C. then commences, with the formation of a clear light amber colored solution noted once 75° C. is achieved. Once 92° C. is achieved, a bright yellow slurry forms. After 2.8 hours at the 100° C. reaction temperature the hot product solution is diluted into 12.7 liters of deionized water, then stirred as a slurry for the next 16 hours, followed by filtration on a coarse fritted glass funnel. After washing the packed bed of light yellow powder on the filter with deionized water, it is removed and dried in the vacuum oven at 100° C. to provide 222.1 grams (99.6 percent isolated yield) of 4,4'-bis[(4-bromophenyl)glyoxalyl]phenyl ether. HPLC analysis reveals the presence of the desired product at 100 area percent.

G) Palladium Catalyzed Coupling of Methyl Acrylate with
4,4'-bis[(4-Bromophenyl)glyoxalyl]phenyl ether 4,4'-bis[(4-Bromophenyl)glyoxalyl]phenyl ether (266.51 grams, 0.45 mole), methyl acrylate (14.05 grams, 0.1632 mole), triethylamine (248.6 grams, 2.457 moles) which had been sparged with dry nitrogen, tri-o-tolylphosphine (2.74 grams, 0.009 mole), palladium (II) acetate (1.01 gram, 0.0045 mole) and N,N-dimethylformamide (2854.5 grams), which has been sparged with dry nitrogen, are added under a dry nitrogen atmosphere to a predried five liter glass three neck round bottom reactor. The reactor is additionally outfitted with an addition funnel topped with a fan cooled spiral condenser, a thermometer with thermostatically controlled heating mantle, and a glass stirring shaft with teflon paddles which is coupled to a variable speed motor to provide mechanical stirring. Additional methyl acrylate (79.61 grams, 0.9247 mole) is added to the addition funnel. Stirring commences with heating to a temperature of 75° C. Dropwise addition of the methyl acrylate commences and is completed after 2.3 hours. After a cumulative 48 hours, HPLC analysis indicates that full conversion of the 4,4'-bis[(4-bromophenyl) glyoxalyl]phenyl ether reactant has been achieved, with no detectable monobromo intermediate present. At this time, the addition funnel is charged with deionized water (225 milliliters) which is added dropwise to the stirred solution, while holding the temperature at 75° C. After completion of this initial water addition, sodium diethyldithiocarbamate trihydrate (10.14 grams, 0.045 mole) is added to the solution in the reactor. After 1.5 hours at the 75° C. temperature, the addition funnel is charged with deionized water (500 milliliters) which is added dropwise to the stirred solution, while holding the temperature at 80° C. After completion of the water addition, heating ceases and the stirred slightly hazy solution is allowed to slowly cool and crystallize over the next 16 hours, followed by vacuum filtration on a medium fritted glass funnel. The packed bed of yellow powder is held on the filter until no further drops of filtrate are observed. The damp cake of product is removed from the filter and charged to a clean five liter glass three neck round bottom reactor outfitted with a glass mechanical stirring rod with polytetrafluoroethylene paddle. Toluene is then added to the reactor (1.5 liters). The reactor is additionally outfitted with a chilled (2° C.) condenser, and a thermometer with thermostatically controlled heating mantle. Stirring and heating to 75° C. commences, then deionized water (750 milliliters) is added to the reactor as a stream, followed by reheating to 75° C. After one hour at 75° C., heating and stirring ceases followed by transfer of the reactor contents to a separatory funnel. The aqueous layer is removed and discarded, followed by addition of the toluene solution back into the reactor, stirring and reheating to 75° C., then addition of a second portion of deionized water (1093 milliliters). After one hour at 85° C., heating and stirring ceases followed by transfer of the reactor contents to a separatory funnel. The aqueous layer is removed and discarded, followed by addition of the toluene solution back into the reactor, stirring and reapplication of heat. Three minutes later, 2-propanol (1.5 liters) is added as a stream to the stirred solution. Once all 2-propanol has been added, the solution is at 40° C. and stirring and heating ceases, with maintenance of the reactor in the heating mantle so as to provide a slow rate of cooling. After standing for 16 hours, the crystalline product which has formed is recovered via vacuum filtration on a medium fritted glass funnel. The product recovered on the funnel is pressed into a hard-packed cake and then sequentially rinsed on the filter with two portions (150 milliliters) of 2-propanol. After drying at 45° C. in the vacuum oven, a 90 percent isolated yield of the methyl acrylate coupling product is recovered as a crystalline light yellow powder. HPLC analysis reveals the presence of the desired product at 100 area percent. Neutron activation analysis of an aliquot of the product reveals the presence of less than one ppm of residual Pd.

H) Hydrogenation of Ethylenic Unsaturation and Hydrolysis of Ester Groups in the Coupling Product Followed by Conversion to the Acid Chloride The product from the palladium catalyzed coupling of methyl acrylate with 4,4'-bis[(4-bromophenyl)glyoxalyl] phenyl ether prepared in G) above is hydrogenated in the manner given in A) above to convert the pair of ethylenically unsaturated hydrocarbon groups to saturated hydrocarbon groups. The pair of ester groups in the resultant diester tetraketone product are hydrolyzed via stirring in a refluxing mixture of 1:1 concentrated hydrochloric acid:deionized water until HPLC analysis of a sample of the product reveals that full conversion of the ester groups to carboxylic acid groups has occurred. The diacid chloride tetraketone product is recovered via rotary evaporation followed by drying in the vacuum oven. The diacid chloride is then prepared in the manner of D) above:

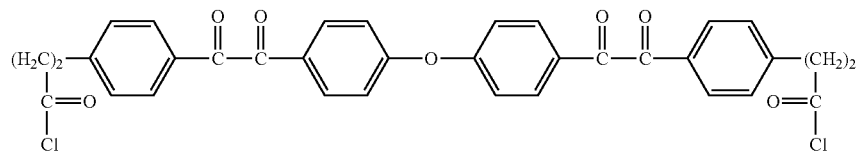

I) Synthesis of Tetraketone Containing Pendant Discotic Moieties

The discotic monoalcohol (0.002 mole) from C) above, anhydrous triethylamine (0.0022 mole) and anhydrous, peroxide-free, tetrahydrofuran (200 milliliters) are added under a dry nitrogen atmosphere to a predried one liter glass three neck round bottom reactor. The reactor is additionally outfitted with magnetic stirring, a fan cooled spiral condenser, a thermometer and an addition funnel charged with 0.001 mole of diacid chloride tetraketone from H) above which has been dissolved in 200 milliliters of anhydrous, peroxide-free, tetrahydrofuran. Dropwise addition of the diacid chloride tetraketone solution to the stirred solution of discotic monoalcohol commences at room temperature and is completed over the next hour. HPLC analysis is used to indicate that full conversion of the reactants has been achieved. The product is then recovered by cooling the stirred solution to 4° C. followed by addition of sufficient deionized water to precipitate the product. The product is recovered via vacuum filtration on a fritted glass funnel, then washed with deionized water on the funnel, then dried in the vacuum oven after vacuum filtration on a fritted glass funnel:

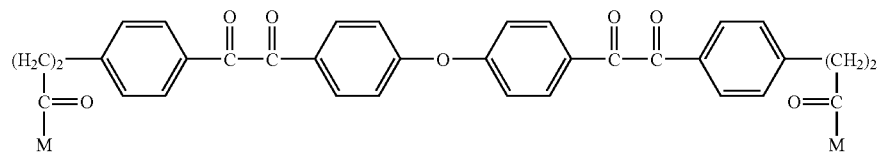

-continued

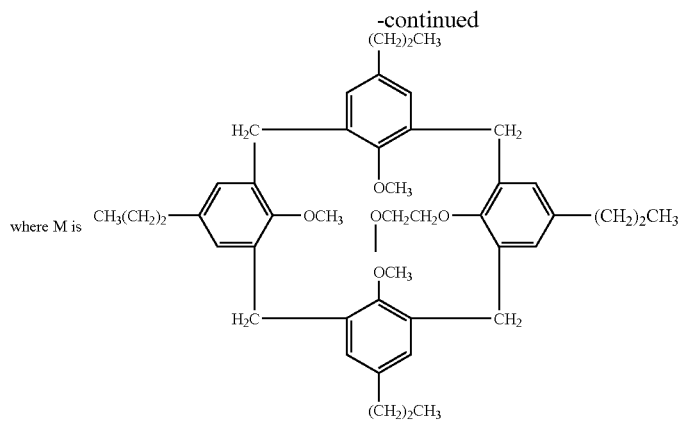

where M is

J) Synthesis of $A_4B_2M_2$ Monomer

A portion of the tetraketone containing pendant discotic moieties (0.01 mole) prepared in the manner of I) above, 1,3-bis(4-phenylethynylphenyl)-2-propanone (0.021 mole), 2-propanol (200 milliliters) and toluene (133 milliliters), are added to a 1 liter four neck Morton flask. The reactor is additionally outfitted with a chilled (2° C.) condenser, a thermometer with thermostatically controlled heating mantle, a Claisen adaptor with addition funnel and nitrogen sparge tube, and a glass stirring shaft with a turbine-type polytetrafluoroethylene stirrer which is coupled to a variable speed motor to provide mechanical stirring. The addition funnel is charged under a dry nitrogen atmosphere with 1M tetrabutylammonium hydroxide in methanol (0.53 milliliter) diluted into 2-propanol (10.5 milliliters). Stirring, sparging with nitrogen (0.3 liter per minute) and heating commences, and once the stirred slurry reaches 80° C., the sparge tube is removed and replaced with an overhead inlet for the nitrogen. Dropwise addition of the solution in the addition funnel to the refluxing stirred slurry commences and is completed over the next 20 minutes, during which time, the yellow slurry is transformed to a deep red solution. HPLC analysis is employed to determine conversion of the reactants, concurrent with optimum formation of the desired double Aldol condensation product and minimum coproduct formation. At the completion of the reaction, heating ceases, the heating mantle is removed from the reactor, additional 2-propanol (180 milliliters) is added to the reactor and the reaction mixture is cooled using a cooling fan on the reactor exterior. Once the stirred slurry cools to 30° C., the product is recovered via filtration through a coarse fritted glass funnel. The crystalline product on the funnel is washed with 2-propanol until a visually clear filtrate is obtained. Drying in a vacuum oven at 60° C. provides a 90 percent isolated yield of the $A_4B_2M_2$ monomer as a purple colored crystalline powder. HPLC analysis demonstrates the presence of greater than 95 area percent of the desired monomer product:

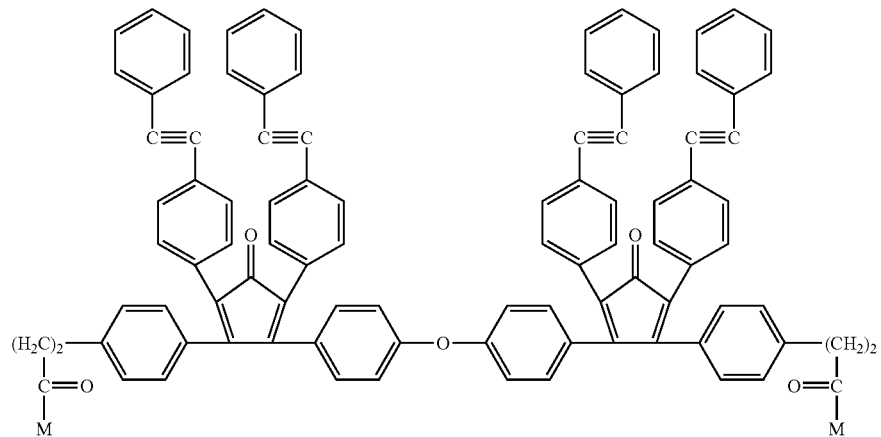

where M is defined in I above

EXAMPLE 2

Preparation of Porous Matrix

To a 50 ml round flask was added 2.0 grams of the $A_4B_2M_2$ monomer from Example 1 J) and 10.0 g of gamma-butyrolactone. The resulting mixture is purged under nitrogen for 15 minutes and then heated to 170° C. with an oil bath under nitrogen for 5 hours. The mixture is then cooled to 145° C. and diluted with 6 grams of cyclohexanone. The mixture is cooled to room temperature to give a suspension of b-staged polymer. The mixture is applied to a silica wafer and cast by spin-coating to form a film having a thickness of about 1.0 µm. The film is baked on a hotplate at 150° C. for 2 minutes, and then transferred to a vacuum oven. The oven temperature is ramped at 7° C. per minute to 415° C. under nitrogen and held at that temperature for 40 minutes to allow the decomposition of discotic mesogen containing poragen before cooling. The resulting film is porous as determined by visual analysis of a photograph obtained by transmission electron microscopy.

EXAMPLE 3

Synthesis of A$_2$BM$_2$ Monomer Containing Rod-like Mesogens

A) Palladium Catalyzed Coupling of Allyl Alcohol with 4,4'-Dibromobenzil

Triphenylphosphine (5.15 mmole), palladium (II) acetate (2.54 mmole) and sodium bicarbonate (764.3 mmole) are added under a dry nitrogen atmosphere to a 500 milliliter glass three neck round bottom reactor. The reactor is additionally outfitted with an addition funnel topped with a fan cooled spiral condenser, a thermometer with thermostatically controlled heating mantle, and magnetic stirring. N,N-Dimethylformamide (100 milliliters) is added to the reactor, and the resultant slurry is stirred for thirty minutes at room temperature, followed by heating to 50° C., then stirring for an additional 15 minutes. Heating to 120° C. commences and once the temperature reaches 80° C., dropwise addition of a solution of 4,4'-dibromobenzil (254.7 mmole) and allyl alcohol (762.7 mmole) in N,N-dimethylformamide (100 milliliters) commences via the addition funnel. Reaction continues at 120° C. until HPLC analysis indicates that full conversion of the 4,4'-dibromobenzil reactant has been achieved, with no detectable monobromo intermediate present. After cooling to room temperature, the reaction mixture is diluted with a mixture of methylethylketone and toluene, then vacuum filtered through a fritted glass funnel to remove salt and precipitated palladium (black). The filtrate is washed three times with deionized water (75 milliliter aliquots), followed by rotary evaporation to recover the product. After drying in the vacuum oven at 50° C., a 90 percent isolated yield of the dialdehyde coupling product is recovered. HPLC analysis reveals the presence of the desired product at 100 area percent.

B) Reduction of Aldehyde Groups to Hydroxyl Groups in the Coupling Product

The product from the palladium catalyzed coupling of allyl alcohol with 4,4'-dibromobenzil prepared in A) above is hydrogenated in the manner given in Example 1, step A) using platinum supported on carbon as the catalyst to convert the pair of aldehyde groups to hydroxyl groups:

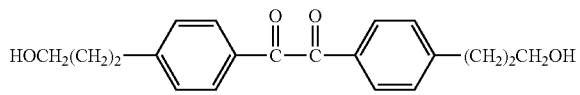

C.) Preparation of Rod-Like Mesogenic Acid Chloride

Bis(4-hydroxyphenyl)terephthalate is prepared substantially according to the method of U.S. Pat. No. 5,270,406. Sufficient benzoyl chloride is then added to a portion of the bis(4-hydroxyphenyl)terephthalate dissolved in anhydrous tetrahydrofuran and using a hydrogen chloride acceptor to provide a mixture containing the maximum amount of monophenol product. The monophenol product is isolated and then reacted with a stoichiometric excess of terephthalyl chloride to provide the monoacid chloride, which is recovered after removal of unreacted terephthalyl chloride. It is also operable to simply react mixtures of benzoyl chloride and terephthalyl chloride with bis(4-hydroxyphenyl)terephthalate, rather than perform the reaction stepwise. Various methods, such as derivatization of a functional group, solvent extraction and chromatography are used to recover the desired monoacid chloride:

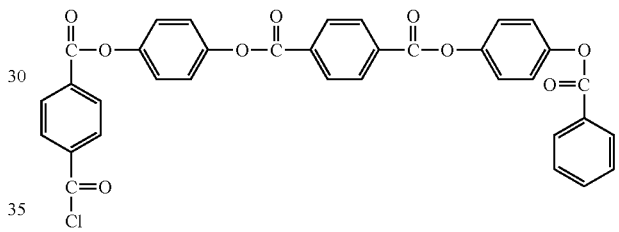

D) Synthesis of Diketone Containing Pendant Rod-Like Mesogenic Moieties

The diketone diol (0.001 mole) from B) above, anhydrous triethylamine (0.0022 mole) and anhydrous, peroxide-free, tetrahydrofuran (100 milliliters) are added under a dry nitrogen atmosphere to a predried one liter glass three neck round bottom reactor. The reactor is additionally outfitted with magnetic stirring, a fan cooled spiral condenser,sa thermometer and an addition funnel charged with 0.002 mole of rod-like mesogenic acid chloride from C) above which has been dissolved in 300 milliliters of anhydrous, peroxide-free, tetrahydrofuran. Dropwise addition of the rod-like mesogenic acid chloride solution to the stirred solution of diketone diol commences at room temperature and is completed over the next hour. HPLC analysis is used to indicate that full conversion of the reactants has been achieved. The product is then recovered by cooling the stirred solution to 4° C. followed by addition of sufficient deionized water to precipitate the product. The product is recovered via vacuum filtration on a fritted glass funnel, washed with deionized water on the funnel, then dried in the vacuum oven after recovery via vacuum filtration on a fritted glass funnel:

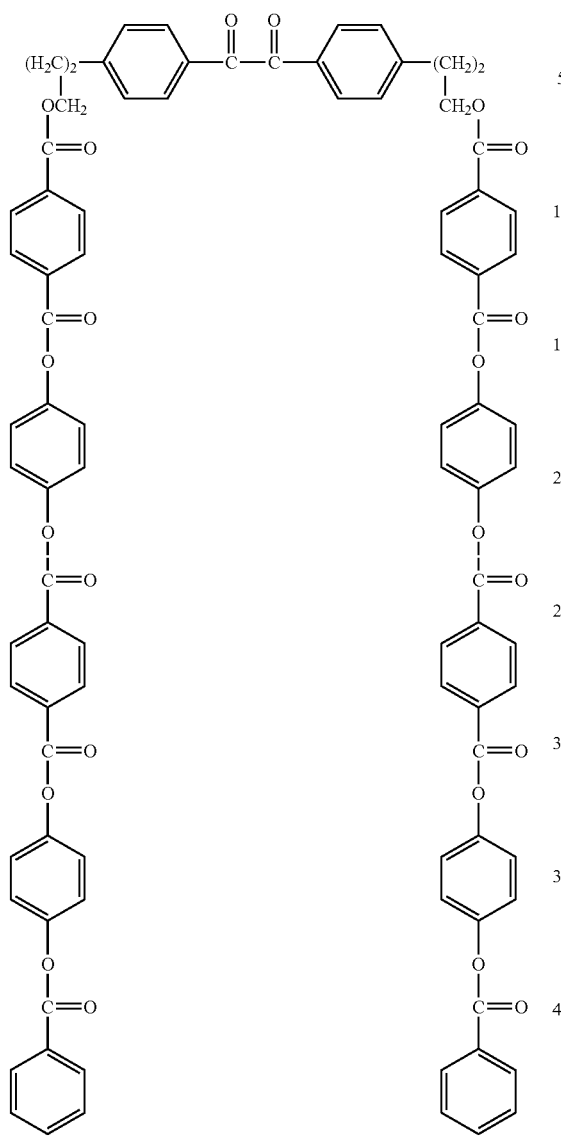

E) Synthesis of A$_2$BM$_2$ Monomer

Diketone containing pendant rod-like mesogenic moieties (0.01 mole) prepared in the manner of D) above, 1,3-bis(4-phenylethynylphenyl)-2-propanone (0.0105 mole), 2-propanol (200 milliliters) and toluene (133 milliliters), are added to a 1 liter four neck Morton flask. The reactor is additionally outfitted with a chilled (2° C.) condenser, a thermometer with thermostatically controlled heating mantle, a Claisen adaptor with addition funnel and nitrogen sparge tube, and a glass stirring shaft with a turbine-type polytetrafluoroethylene stirrer which is coupled to a variable speed motor to provide mechanical stirring. The addition funnel is charged under a dry nitrogen atmosphere with 1M tetrabutylammonium hydroxide in methanol (0.27 milliliter) diluted into 2-propanol (5.3 milliliters). Stirring, sparging with nitrogen (0.3 liter per minute) and heating commences, and once the stirred slurry reaches 80° C., the sparge tube is removed and replaced with an overhead inlet for the nitrogen. Dropwise addition of the solution in the addition funnel to the refluxing stirred slurry commences and is completed over the next 10 minutes, during which time, the yellow slurry is transformed to a deep red solution. HPLC analysis is employed to determine conversion of the reactants, concurrent with optimum formation of the desired Aldol condensation product and minimum coproduct formation. At the completion of the reaction, heating ceases, the heating mantle is removed from the reactor, additional 2-propanol (180 milliliters) is added to the reactor and the reaction mixture is cooled using a cooling fan on the reactor exterior. Once the stirred slurry cools to 30° C., the product is recovered via filtration through a coarse fritted glass funnel. The crystalline product on the funnel is washed with 2-propanol until a visually clear filtrate is obtained. Drying in a vacuum oven at 60° C. provides a 90 percent isolated yield of the A$_2$BM$_2$ monomer as a purple colored crystalline powder. HPLC analysis demonstrates the presence of greater than 95 area percent of the desired monomer product:

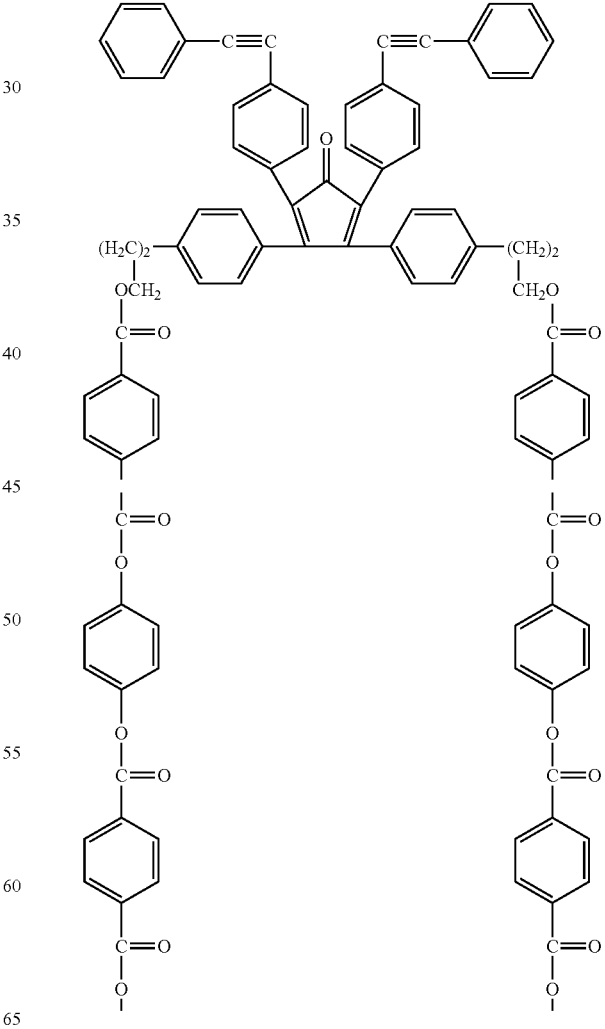

-continued

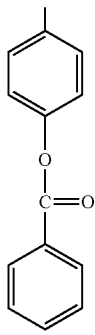
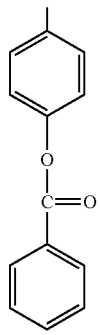

EXAMPLE 4

Preparation of Porous Matrix

To a 50 ml round flask was added 2.0 grams of the $A_2BM_2$ monomer from Example 3 E) and 20.0 g of gamma-butyrolactone. The resulting mixture is purged under nitrogen for 15 minutes and then heated to 170° C. with an oil bath under nitrogen for 5 hours. The mixture is then cooled to 145° C. and diluted with 12 grams of cyclohexanone. The mixture is cooled to room temperature to give a suspension of b-staged polymer. The mixture is applied to a silica wafer and cast by spin-coating to form a film having a thickness of about 1.0 μm. The film is baked on a hotplate at 150° C. for 2 minutes, and then transferred to a vacuum oven. The oven temperature is ramped at 7° C. per minute to 415° C. under nitrogen and held at that temperature for 40 minutes to allow the decomposition of discotic mesogen containing poragen before cooling. The resulting film is porous as determined by visual analysis of a photograph obtained by transmission electron microscopy.

What is claimed is:

1. A compound corresponding to the formula,

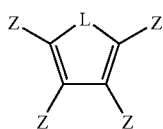

(I)

wherein L is —O—, —S—, —N=N—, —C(O)—, —(SO$_2$)—, or —OC(O)—;

Z is independently in each occurrence hydrogen, halogen, an unsubstituted or inertly substituted hydrocarbyl group, Z"X, or two adjacent Z groups together with the carbons to which they are attached form a fused aromatic ring, Z" is a divalent derivative of an unsubstituted or inertly substituted hydrocarbyl group joining two or more structures of formula (I), or joining a dienophile group, a bound mesogenic poragen forming moiety, or a moiety comprising both an A-functionality and a bound mesogenic poragen forming moiety, X is a second structure of formula (I), a moiety comprising a dienophile group, a group comprising a mesogenic poragen forming moiety, or a moiety comprising both a dienophile group and a mesogenic poragen forming moiety and in at least one occuffence, Z is a Z"X group of the formula: -Z"-C≡CM; or in at least one occurrence, Z is a Z"X group of the formula: -Z"-C≡CR and in at least one other occurrence Z is a Z"X group comprising a mesogenic poragen forming moiety; wherein, M is independently each occurrence a bound mesogenic poragen forming moiety; and R is independently each occurrence selected from the group consisting of hydrogen, $C_{1-4}$ alkyl, $C_{6-60}$ aryl, and $C_{7-60}$ inertly substituted aryl groups.

2. A compound according to claim 1 corresponding to the formula:

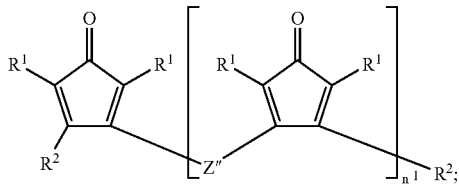

wherein $R^1$ independently each occurrence is $C_{6-20}$ aryl, $C_{6-20}$ inertly substituted aryl, or $R^2$;

$R^2$ is $C_{6-20}$ aryl-substituted ethynyl, -Z"-M, $C_{6-20}$ aryl, or $C_{6-20}$ inertly substituted aryl;

Z" is a divalent linking group, and

M is a bound mesogenic poragen forming moiety, $n^1$ is a number greater than or equal to zero;

with the proviso that in at least one occurrence $R^1$ or $R^2$ is $C_{6-20}$ aryl-substituted ethynyl, and in at least one other occurrence $R^1$ or $R^2$ is -Z"-M.

3. A compound according to claim 2 wherein $R^1$ and $R^2$ groups are independently selected from the group consisting of: $C_{6-20}$ aryl-substituted ethynyl, -Z"-M, —C≡C-M, $C_{6-20}$ aryl, and inertly substituted $C_{6-20}$ aryl;

Z" is selected from the group consisting of: phenylene, biphenylene, phenyleneoxyphenylene, ethynylene, -phenylene-C$_{1-12}$ alkylene-, -phenylene-O—C$_{1-12}$ alkylene-, -phenylene-C$_{1-12}$ alkylene-O—, -phenylene-O—C$_{1-12}$ alkylene-O—, -phenylene-CO—, -phenylene-O—, -phenylene-OC(O)—, -phenylene-C(O)O—, -phenylene-C(O)—NH—, -phenylene-NH—C(O)—, -phenylene-OC(O)O—, -phenylene-NHC(O)O—, -phenylene-OC(O)NH—, -phenylene-NHC(O)NH—, -phenylene-C$_{1-12}$ alkylene-C(O)O—, -phenylene-C$_{1-12}$ alkylene-C(O)NH—, -phenylene-C$_{1-12}$ alkylene-OC(O)—, -phenylene-C$_{1-12}$ alkylene-OC(O)NH—, -phenylene-C$_{1-12}$ alkylene-NHC(O)O—, -phenylene-C$_{1-12}$ alkylene-OC(O)O—, -phenylene-C$_{1-12}$ alkylene-NHC(O)NH—, -phenylene-O—C$_{1-12}$ alkylene-C(O)O—, -phenylene-O—C$_{1-12}$ alkylene-C(O)NH—, -phenylene-O—C$_{1-12}$ alkylene-OC(O)—,-phenylene-O—C$_{1-12}$ alkylene-OC(O)NH—, -phenylene-O—C$_{1-12}$ alkylene-NHC(O)O—, -phenylene-O—C$_{1-12}$ alkylene-OC(O)O— and -phenylene-O—C$_{1-12}$ alkylene-NHC(O)NH—; and M is a discotic mesogenic poragen forming moiety.

4. A cross-linked polymer formed by curing a composition comprising a compound according to claim 1.

5. A porous matrix formed by removing of self-assembled poragens formed from bound mesogenic poragen forming moieties in the cross-linked polymer of claim 4.

* * * * *

UNITED STATES PATENT AND TRADEMARK OFFICE
CERTIFICATE OF CORRECTION

PATENT NO. : 7,585,928 B2
APPLICATION NO. : 10/575992
DATED : September 8, 2009
INVENTOR(S) : Robert E. Hefner, Jr.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 442 days.

Signed and Sealed this

Fourteenth Day of September, 2010

David J. Kappos
*Director of the United States Patent and Trademark Office*